(12) United States Patent
Qin

(10) Patent No.: US 9,963,433 B2
(45) Date of Patent: May 8, 2018

(54) ANTICANCER DRUGS INCLUDING THE CHEMICAL STRUCTURES OF AN ANDROGEN RECEPTOR LIGAND AND A HISTONE DEACETYLASE INHIBITOR

(71) Applicant: Wayne State University, Detroit, MI (US)

(72) Inventor: Zhihui Qin, Mundelein, IL (US)

(73) Assignee: Wayne State University, Detroit, MI (US)

( * ) Notice: Subject to any disclaimer, the term of this patent is extended or adjusted under 35 U.S.C. 154(b) by 0 days. days.

(21) Appl. No.: 15/417,860

(22) Filed: Jan. 27, 2017

(65) Prior Publication Data

US 2017/0217903 A1 Aug. 3, 2017

Related U.S. Application Data

(60) Provisional application No. 62/288,810, filed on Jan. 29, 2016.

(51) Int. Cl.
*C07D 233/86* (2006.01)
*A61K 31/4178* (2006.01)
*A61K 31/4166* (2006.01)
*C07F 9/6506* (2006.01)
*C07D 401/12* (2006.01)

(52) U.S. Cl.
CPC ........ *C07D 233/86* (2013.01); *A61K 31/4166* (2013.01); *A61K 31/4178* (2013.01); *C07D 401/12* (2013.01); *C07F 9/65061* (2013.01)

(58) Field of Classification Search
None
See application file for complete search history.

(56) References Cited

U.S. PATENT DOCUMENTS

| | | | |
|---|---|---|---|
| 7,709,517 B2 | 5/2010 | Sawyers et al. | |
| 8,183,274 B2 | 5/2012 | Sawyers et al. | |
| 8,470,829 B2 * | 6/2013 | Tachibana | C07D 211/58 514/254.05 |
| 9,126,941 B2 | 9/2015 | Sawyers et al. | |
| 9,139,565 B2 | 9/2015 | Oyelere et al. | |
| 9,517,229 B2 * | 12/2016 | Protter | A61K 31/4184 |
| 9,586,947 B2 * | 3/2017 | Lu | C07D 233/86 |
| 2016/0214972 A1 * | 7/2016 | Jin | C07D 417/12 |

OTHER PUBLICATIONS

Jung, Michael E. Structure-Activity Relationship for Thiohydantoin Androgen Receptor Antagonists for Castration-Resistant Prostate Cancer (CRPC). J. Med. Chem. 2010, 53, 2779-2796.*
Balbas, et al., "Overcoming mutation-based resistance to antiandrogens with rational drug design," Elife 2, 2013, e00499.
Bali, et al., "Inhibition of Histone Deacetylase 6 Acetylates and Disrupts the Chaperone Function of Heat Shock Protein 90: A Novel Basis for Antileukemia Activity of Histone Deacetylase Inhibitors," J. Biol. Chem., vol. 280, No. 29, 2005, pp. 26729-26734.
Basak, et al., "Genistein down-regulates androgen receptor by modulating HDAC6-Hsp90 chaperone function," Mol. Cancer Ther., vol. 7, No. 10, 2008, pp. 3195-3202.
Beer, et al., "Enzalutamide in Metastatic Prostate Cancer before Chemotherapy," N. Engl. J. Med., vol. 371, No. 5, 2014, pp. 424-433.
Bhat, et al., "Progress in the Discovery and Development of Heat Shock Protein 90 (Hsp90) Inhibitors," J. Med. Chem., vol. 57, No. 21, 2014, pp. 8718-8728.
Bradley, et al., "Vorinostat in Advanced Prostate Cancer Patients Progressing on Prior Chemotherapy (NCI Trial #6862): Trial results and IL-6 analysis. A study by the DOD Prostate Cancer Clinical Trial Consortium and University of Chicago Phase II Consortium," Cancer, vol. 115, No. 23, 2009, pp. 5541-5549.
Burdelski, et al., "HDAC1 overexpression independently predicts biochemical recurrence and is associated with rapid tumor cell proliferation and genomic instability in prostate cancer," Exp. Mol. Pathol., vol. 98, No. 3, 2015; pp. 419-426.
Chen, et al., "Antiandrogens and androgen depleting therapies in prostate cancer: novel agents for an established target," Lancet Oncol., vol. 10, No. 10, 2009, pp. 981-991.
Chen, et al., "Chemical ablation of androgen receptor in prostate cancer cells by the histone deacetylase inhibitor LAQ824," Mol. Cancer Ther., vol. 4, No. 9, 2005, pp. 1311-1319.
Chen, et al., "Computational Exploration of Zinc Binding Groups for HDAC Inhibition," J. Org. Chem., vol. 78, No. 10, 2013, pp. 5051-5055.
Eigl, et al., "A phase II study of the HDAC inhibitor SB939 in patients with castration resistant prostate cancer: NCIC clinical trials group study IND195," Invest New Drugs, vol. 33, No. 4, 2015, pp. 969-976.
Fang, et al., "Hsp90 Regulates Androgen Receptor Hormone Binding Affinity in Vivo," J. Bio. Chem., vol. 271, No. 45, 1996, pp. 28697-28702.
Gibbs, et al., "Tropical forests were the primary sources of new agricultural land in the 1980s and 1990s," PNAS, vol. 107, No. 38, 2010, pp. 16732-16737.
Gravina, et al., "PXD101 potentiates hormonal therapy and prevents the onset of castration-resistant phenotype modulating androgen receptor, HSP90, and CRM1 in preclinical models of prostate cancer," Endocrine Related Cancer, vol. 20, 2013, pp. 321-337.
Gryder, et al., "Selectively targeting prostate cancer with antiandrogen equipped histone deacetylase inhibitors," ACS Chem. Biol., vol. 8, No. 11, 2013, 23 pages.
Guerrero, et al., "Enzalutamide, an androgen receptor signaling inhibitor, induces tumor regression in a mouse model of castration-resistant prostate cancer," The Prostate, vol. 73, No. 12, 2013, pp. 1291-1305.
He, et al., "Potent activity of the Hsp90 inhibitor ganetespib in prostate cancer cells irrespective of androgen receptor status or variant receptor expression," Int. J. Oncol., vol. 42, 2013, pp. 35-43.
Heath, et al., "A Phase II Trial of 17-Allylamino-17-Demethoxygeldanamycin (17-AAG) in Patients with Hormone-Refractory Metastatic Prostate Cancer," Clin. Cancer Res., vol. 14, No. 23, 2008, pp. 7940-7946.

(Continued)

*Primary Examiner* — Samantha L Shterengarts
(74) *Attorney, Agent, or Firm* — Lee & Hayes PLLC; C. Rachal Winger

(57) ABSTRACT

A novel class of drugs for treating androgen receptor (AR) positive cancer including prostate cancer and breast cancer are described. The drugs include the chemical scaffolds of a high affinity androgen receptor ligand and a histone deacetylase inhibitor. Also described are compositions including the novel drugs and methods of treating AR positive cancer using the compositions.

12 Claims, 6 Drawing Sheets

(56) References Cited

OTHER PUBLICATIONS

Kovacs, et al., "HDAC6 Regulates Hsp90 Acetylation and Chaperone-Dependent Activation of Glucocorticoid Receptor," Molecular Cell, vol. 18, 2005, pp. 601-607.
Liu, et al., "KU675, a Concomitant Heat-Shock Protein Inhibitor of Hsp90 and Hsc70 that Manifests Isoform Selectivity for Hsp90alpha in Prostate Cancer Cells," Mol. Pharmacol., vol. 88, 2015, pp. 121-130.
Marrocco, et al., "Suberoylanilide hydroxamic acid (vorinostat) represses androgen receptor expression and acts synergistically with an androgen receptor antagonist to inhibit prostate cancer cell proliferation," Mol. Cancer Ther., vol. 6, No. 1, 2007, pp. 51-60.
Molife, et al., "Phase II, two-stage, single-arm trial of the histone deacetylase inhibitor (HDACi) romidepsin in metastatic castration-resistant prostate cancer (CRPC)," Annals of Oncology, vol. 21, 2010, pp. 109-113.
Neckers and Workman, "Hsp90 molecular chaperone inhibitors: are we there yet?" Clin. Cancer Res., vol. 18, No. 1, 2012, pp. 64-76.
Oh, et al., "Multicenter Phase 2 Trial of the Hsp-90 Inhibitor, IPI-504 (retaspimycin hydrochloride), in Patients with Castration-Resistant Prostate Cancer," Urology, vol. 78, No. 3, 2011, pp. 626-630.
Pacey, et al., "A Phase I study of the Heat Shock Protein 90 inhibitor alvespimycin (17-DMAG) given intravenously to patients with advanced solid tumors," Clin. Cancer Res., vol. 17, No. 6, 2011, pp. 1561-1570.
Rathkopf, et el., "A Phase 2 Study of Intravenous Panobinostat in Patients With Castration-Resistant Prostate Cancer," Cancer Chemother. Pharmacol., vol. 72, No. 3, 2013, pp. 537-544.
Ratnam, et al., "Mechanisms of ARE-Independent Gene Activation by the Androgen Receptor in Prostate Cancer Cells: Potential Targets for Better Intervention Strategies," Androgen-Responsive Genes in Prostate Cancer, Springer, 2013, pp. 85-100.
Saporita, et al., "The Hsp90 inhibitor, 17-AAG, prevents the ligand-independent nuclear localization of androgen receptor in refractory prostate cancer cells," The Prostate, vol. 67, No. 5, 2007, pp. 509-520.
Sato, et al., "Vorinostat and Bortezomib Synergistically Cause Ubiquitinated Protein Accumulation in Prostate Cancer Cells," J. Urology, vol. 188, No. 6, 2012, pp. 2410-2418.
Scher, et al., "Increased Survival with Enzalutamide in Prostate Cancer after Chemotherapy," N. Engl. J. Med., vol. 367, 2012; pp. 1187-1197.
Solit, et al., "17-Allylamino-17-demethoxygeldanamycin Induces the Degradation of Androgen Receptor and HER-2/neu and Inhibits the Growth of Prostate Cancer Xenografts," Clinical Cancer Res., vol. 8, No. 5, 2002, pp. 986-993.
Thakur, et al., "A phase II trial of ganetespib, a heat shock protein 90 Hsp90) inhibitor, in patients with docetaxel-pretreated metastatic castrate-resistant prostate cancer (CRPC)—a prostate cancer clinical trials consortium (PCCTC) study," Invest. New Drugs., vol. 34, No. 1, 2016, pp. 112-118.
Tran, et al., "Development of a second-generation antiandrogen for treatment of advanced prostate cancer," Science, vol. 324, 2009, pp. 787-790.
Veldscholte, et al., "Hormone-induced dissociation of the androgen receptor-heat-shock protein complex: use of a new monoclonal antibody to distinguish transformed from nontransformed receptors," Biochemistry, 1992, vol. 31, No. 32, pp. 7422-7430.
Weichert, et al., "Histone deacetylases 1, 2 and 3 are highly expressed in prostate cancer and HDAC2 expression is associated with shorter PSA relapse time after radical prostatectomy," British Journal of Cancer, vol. 98, 2008, pp. 604-610.
Welsbie, et al., "Histone Deacetylases Are Required for Androgen Receptor Function in Hormone-Sensitive and Castrate-Resistant Prostate Cancer," Cancer Research, vol. 69, No. 3, 2009, pp. 958-966.
Zhou, et al., "Preclinical evaluation of combined antineoplastic effect of DLC1 tumor suppressor protein and suberoylanilide hydroxamic acid on prostate cancer cells," Biochem. Biophys. Res. Commun., vol. 420, No. 2, 2012, pp. 325-330.

* cited by examiner

ANTICANCER DRUGS INCLUDING THE CHEMICAL STRUCTURES OF AN ANDROGEN RECEPTOR LIGAND AND A HISTONE DEACETYLASE INHIBITOR

CROSS REFERENCE TO RELATED APPLICATION

This application claims priority to U.S. Provisional Patent Application No. 62/288,810, filed on Jan. 29, 2016, which is incorporated herein by reference in its entirety as if fully set forth herein.

STATEMENT OF GOVERNMENT SUPPORT

This invention was made with Government support under Grant No. W81XWH-12-1-0340 awarded by the U.S. Department of Defense. The Government has certain rights in this invention.

FIELD OF THE DISCLOSURE

The present disclosure provides a novel class of drugs for the treatment of androgen receptor (AR) positive cancers. The drugs include parts of the chemical structures of an androgen receptor ligand and a histone deacetylase inhibitor.

BACKGROUND OF THE DISCLOSURE

Cancer (neoplasia) is characterized by deregulated cell growth and cell division. There are numerous types of cancers. Examples of cancers include prostate cancer and breast cancer.

Prostate cancer, as its name indicates, is a cancer that develops in the prostate gland of the male reproductive system. Prostate cancer can be aggressive, in which cancer cells metastasize and move from the prostate gland to other parts of the body, such as the lymph nodes and the bones. It is the second leading cause of cancer-related death in men in the U.S., and its prevalence is increasing in developing countries.

Prostate cancer growth is often driven by male sex hormones called androgens, which include testosterone. Because of this, a common treatment option for the 22% or 35,200 patients that cannot be treated with surgery, radiation, cryotherapy or watchful waiting is to lower the levels of androgens in the man's body. Androgen levels can be lowered by surgically removing the testicles or with drugs that stop the testicles, and to a lesser extent adrenal glands, from making androgens or block how they affect the body. This type of treatment is called hormonal therapy or androgen-deprivation therapy. Unfortunately, 40,000 patients each year begin to fail hormonal therapy or become hormone refractory. That is, they develop castration-resistant prostate cancer (CRPC) or hormone refractory prostate cancer (HRPC). Nevertheless, CRPC tumors typically continue to produce the androgen receptor (AR). CRPC tumors may continue to depend on AR for growth by producing greatly elevated levels of AR or by producing variant forms of AR in addition to the normal AR. Treatment options for prostate cancer are very limited once the disease becomes resistant to hormonal therapy through these or any other mechanisms.

Breast cancer is the fifth most common cause of cancer death in the world. In the U.S., breast cancer is the most common cancer diagnosed in women, and the second most common cause of cancer death in women. The treatment of breast cancer depends on various factors including stage of the cancer and age of the patient. Breast cancer is usually treated with surgery, such as lumpectomy or mastectomy followed by medication and/or radiation therapy. Medication includes hormone-blocking agents, chemotherapeutic agents, and monoclonal antibodies.

Although the focus of breast cancer research has been on estrogen receptor a (ER) signaling, androgens are known to play a role in normal breast physiology and therefore androgen receptor (AR) signaling is recognized as an important contributor towards breast carcinogenesis. Moreover, it appears that AR is expressed in many breast cancers, which makes AR an attractive therapeutic target.

SUMMARY OF THE DISCLOSURE

The current disclosure provides a novel class of drugs that is synthesized by combining the partial chemical scaffolds of a high affinity androgen receptor ligand and a histone deacetylase inhibitor. The current disclosure also provides compositions including the novel drugs and methods of using the compositions to treat androgen receptor positive cancers such as prostate cancer and breast cancer.

Figure 4A:
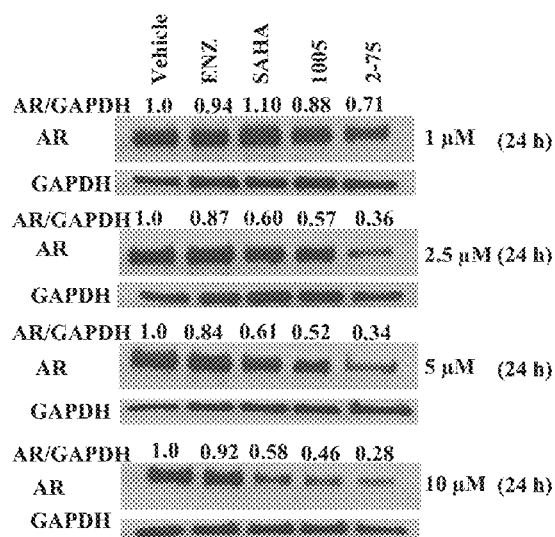
Figure 4B:
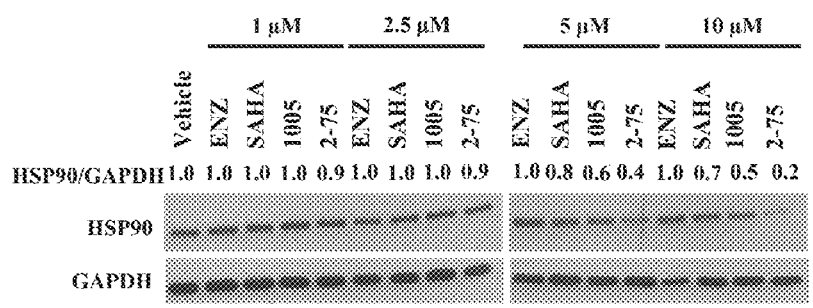
Figure 4C:
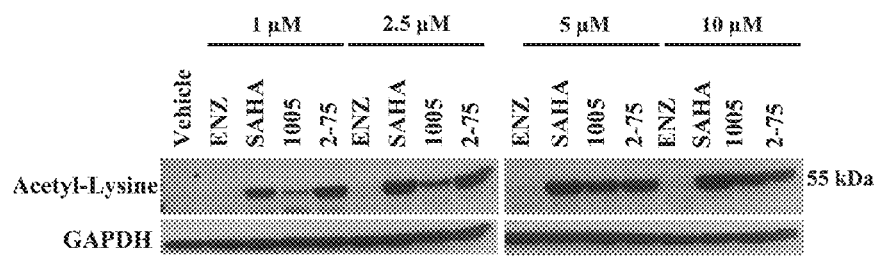

FIGS. 4A-4C show induction of protein degradation and hyper-acetylation. C4-2 cells were treated with the indicated concentrations of Enz, SAHA, 1005 or 2-75 or with vehicle (DMSO) for 24 h. Cells were then harvested for western blot analysis using antibody to AR (4A), HSP90 (4B), Acetyl-Lysine (4C) or GAPDH (loading control). ImageJ software was used to determine the intensities of the bands relative to the vehicle control for each protein. The values were then divided by the values for GAPDH within the same samples.

Figure 5A:
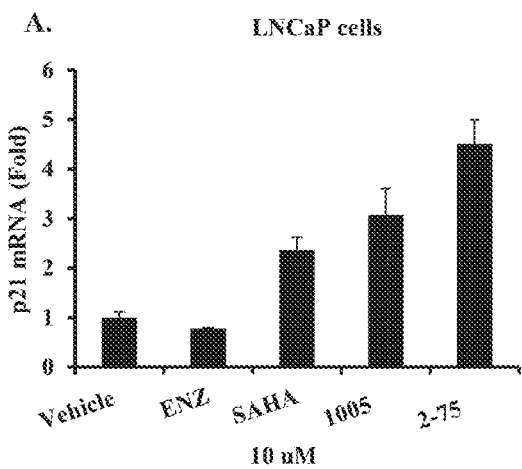
Figure 5B:
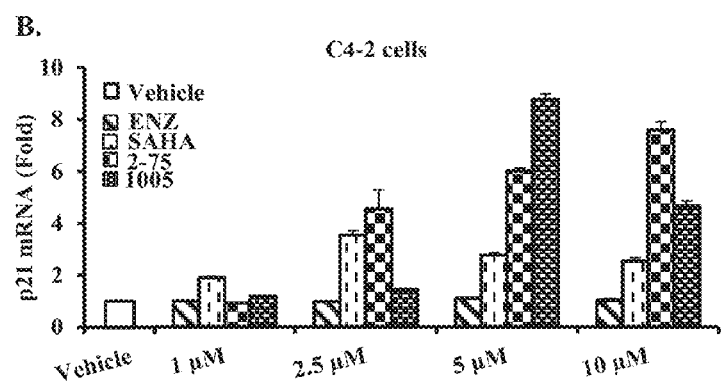
Figure 5C:
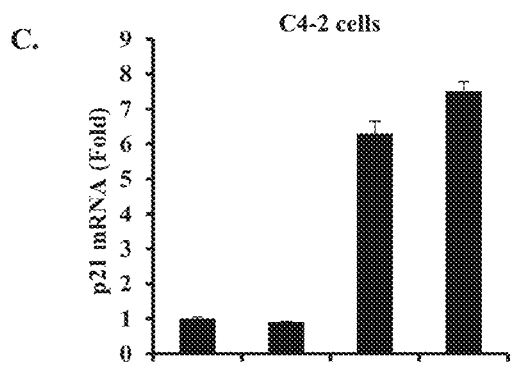

FIGS. 5A-5C show induction of p21 mRNA. (5A) LNCaP cells were treated with Enz, SAHA, 1005 or 2-75 at a concentration of 10 µM or with vehicle (DMSO) for 48 h. Cells were then harvested to quantify p21 mRNA and the values were normalized to those for GAPDH mRNA. (5B) C4-2 cells were treated with Enz, SAHA, 1005 or 2-75 at the indicated concentrations or with vehicle (DMSO) for 48 h. Cells were then harvested to quantify p21 mRNA and the values were normalized to those for GAPDH mRNA. (5C) C4-2 cells were treated with either Enz (10 µM) or SAHA (10 µM), or an equimolar (10 µM each) mixture of Enz and SAHA. Cells were then harvested to quantify p21 mRNA, and the values were normalized to those for GAPDH mRNA. In all panels (5A-5C), the error bars represent standard deviation of experimental triplicates. *P<0.001.

FIGS. 6A-6E show the effects on cell viability in Enz-resistant standard CRPC model cells. (6A) C4-2 cells were seeded in 96-well plates and 24 h later, they were treated with the indicated compounds (0.1 µM-10 µM) or with vehicle (DMSO). Cell viability was measured by the MTT assay on Days 0 and 3 of treatment. $EC_{50}$ values were calculated from nonlinear regression plots using GraphPad Prism5 software. (6B) C4-2 cells were seeded and treated 24 h later with Enz (2.5 µM), SAHA (2.5 µM), an equimolar mixture of Enz and SAHA (each compound at 2.5 µM), 2-75 (2.5 µM) or with vehicle (DMSO). Cell viability was measured by the MTT assay on Days 0 and 3 of treatment. (6C) C4-2 cells were seeded and treated 24 h later with SAHA (5 µM), 2-75 (5 µM), 1005 (5 µM) or with vehicle (DMSO). Cell viability was measured by the MTT assay on Days 0 and 3 of treatment. The data in (6C) is plotted as percent viability on Day 3 relative to Day 0 to illustrate the fact that the treatments caused cell death. (6D) 22Rv1 cells were infected with AR shRNA lentivirus, or control shRNA. 72 h after infection, cells were plated and viable cells were measured by the MTT assay on the indicated days (6D, bottom). Cells were also harvested for western blot analysis and probed with antibody to AR, which was also reactive with the AR splice variant AR-V7 (6D, top). (6E) 22Rv1 cells were seeded in 96-well plates and 24 h later, they were treated with the indicated compounds (0.1 µM-10 µM) or with vehicle (DMSO). Cell viability was measured by the MTT assay on Days 0 and 3 of treatment. $EC_{50}$ values were calculated from nonlinear regression plots using GraphPad Prism5 software. In all panels (6A-6E), the error bars represent standard deviation of experimental sextuplicate samples. *P<0.001.

DETAILED DESCRIPTION

Prostate cancer (PCa) is the second leading cause of cancer-related deaths in men in the United States (Siegel et al., 2015). PCa is initially managed with surgery, radiation, androgen antagonists (e.g., bicalutamide) and surgical or chemical castration. However, the relapsed or metastatic disease post-castration (castration-recurrent prostate cancer or CRPC) has poor prognosis with most patients dying within 2 years (Karantanos et al., 2015). Innovative treatment approaches are urgently needed to treat CRPC patients.

Over the years research in breast cancer has focused on the dominant sex hormone in females, that is, estrogens. However, because male sex hormones also play a role in normal female breast physiology, research has also been conducted in the use of androgens for breast cancer therapy. Moreover, the high frequency of AR expression in breast cancer makes it an attractive therapeutic target.

AR signaling is a major driving force in all stages of PCa (Chen et al., 2009). CRPC cells evolve mechanisms to re-activate AR signaling under androgen deprivation conditions (Mitsiades, 2013); these mechanisms include overexpression and gain-of-function mutations of AR (Joseph et al., 2013; Korpal et al., 2013), overexpression of AR splice variants (AR-Vs) (Li et al., 2013), compensatory cross-talk between AR and other signaling pathways (Liu et al., 2014) and enhanced intra-tumoral androgen biosynthesis (Nakamura et al., 2005). Enzalutamide (Enz, FIG. 1A) is a newly FDA approved AR antagonist that prolongs survival of CRPC patients (Beer et al., 2014; Scher et al., 2012). Enz competitively binds to AR with 5-8 fold higher affinity than bicalutamide and, in contrast to bicalutamide, does not promote AR nuclear translocation (Tran et al., 2009). Nevertheless, acquired resistance to Enz typically develops within months and is associated with a relatively short-lived patient survival benefit. Indeed, well established CRPC cell line models that either vastly overexpress AR (e.g., C4-2 cells) or over-express AR splice variants (e.g., 22Rv1 cells), presumably in combination with changes in other cellular signaling pathways, are completely resistant to Enz while remaining addicted to AR. Therefore, drugs that can more effectively antagonize AR signaling in CRPC cells are desirable.

Histone deacetylases (HDACs) are validated drug targets for CRPC treatment. The balance of histone acetylation and deacylation is critical in the regulation of gene expression. Histone acetylation induced by histone acetyl transferases (HATs) is associated with gene transcription, while histone hypoacetylation induced by histone deacetylase (HDAC) activity is associated with gene silencing. Altered expression and mutations of genes that encode HDACs have been linked to tumor development since they both induce the aberrant transcription of key genes regulating important cellular functions such as cell proliferation, cell cycle regulation, and apoptosis.

HDAC inhibitors (HDACis) have been shown to inhibit the proliferation of tumor cells in culture and in vivo by inducing cell cycle arrest, differentiation and/or apoptosis. HDACis exert their anti-tumor effects via the induction of expression changes of oncogenes or tumor suppressors through modulating the acetylation/deacetylation of histones and/or non-histone proteins as well as other proteins.

An example of a HDACi is suberanilohydroxamic acid (SAHA, FIG. 1B), which is also known as vorinostat. SAHA has been shown to bind to the active site of HDACs, and its hydroxamic acid functional group acts as a chelator for zinc ion which is also found in the active site of HDAC. The inhibition of HDACs by SAHA results in the accumulation of acetylated histones and acetylated proteins, including transcription factors crucial for the expression of genes needed to induce cell differentiation. SAHA is a FDA approved drug for treating hematological cancers.

HDACi can inhibit viability of PCa cells through several mechanism including degradation of the AR by modifying its cytosolic chaperone Hsp90. However, dose limiting and long-term toxicities associated with their pleiotropic effects render HDACi ineffective in PCa treatment. Accordingly, although HDACs are validated drug targets for CRPC treatment, all clinically tested HDACis have only been shown to have modest or inferior outcomes because in addition to disrupting AR they also interfered with many other actions of HDACs causing toxicities that limited their use at high enough doses or for durations long enough to provide substantial clinical benefit. Therefore, there is a need to provide new drugs that are more effective than Enz for the treatment of CRPC including Enz resistant CRPC that have acceptable toxicity profiles compared to HDACis.

The current disclosure describes a new class of androgen receptor targeted compounds that can be used to effectively treat AR positive cancers including advanced prostate cancer and breast cancer. These new compounds have been synthesized to include partial chemical scaffolds of an AR ligand, for example Enz, and a HDACi, for example SAHA. As mentioned above, Enz is a high affinity androgen receptor ligand and SAHA is a HDACi. Accordingly, this new class of compounds retains the binding to AR with high affinity and potentiates only the specific HDACi activity of disrupting AR or proteins associated with AR. In contrast to known drugs, the use of the Enz scaffold avoids drug-stimulated nuclear translocation of AR and selectively amplifies the action of HDACi on proteins at the site of AR stores in the cytosolic compartment. Moreover, the compounds have weaker intrinsic pan-HDACi activities compared to their parent HDACi. These properties limit the range of HDACi targets and reduce toxicity. These compounds are as effective, if not more effective, compared with the more potent parent HDACi, in inhibiting the growth and the killing of CRPC cells that are completely resistant to Enz. By depending on AR to target other critical AR-associated proteins such as heat shock protein 90 (Hsp90), these compounds are selective for the AR producing prostate cancer cells compared with Hsp90 inhibitor drugs that would have undesirable effects on normal tissues that have absent or low amounts of AR.

Hsp90 is a chaperone protein that assists other proteins to fold properly, stabilizes proteins against heat stress, and aids in protein degradation. It also stabilizes a number of proteins required for tumor growth. Hsp90 inhibition is important for prostate cancer because Hsp90 is overexpressed in prostate cancer cells compared with normal prostate epithelium and thus provides a potential selective target. Many Hsp90 client proteins have known roles in prostate carcinogenesis. Examples of such client proteins include AR, HER2, EGRF, CDK4, and AKT.

The new class of compounds provided herein have the following structural formula:

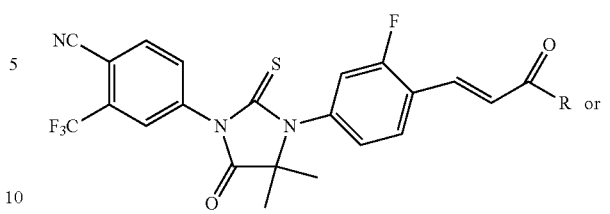

Formula (I)

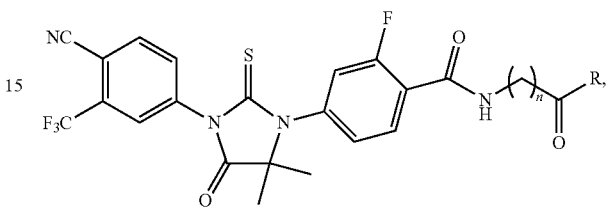

Formula (II)

wherein:
n is 1 to 10; and
R is a hydrogen atom, a halogen atom, a hydroxyl group, a nitro group, an amino group, an alkyl group, a cycloalkyl group, an alkenyl group, an alkynyl group, an alkoxy group, an aryl group, an aralkyl group, or a heterocyclic group.

The current disclosure also provides salts, solvates, hydrates, N-oxides, prodrugs, and active metabolites of the compounds of Formula (I) or Formula (II). As used herein, the term "drug" refers to a compound of Formula (I) or (II), or a salt, solvate, hydrate, N-oxide, prodrug, or active metabolite of a compound of Formula (I) or (II).

Suitable acid addition salts of the compounds disclosed herein can be prepared from an inorganic acid or an organic acid, in particular pharmaceutically acceptable organic acid. Examples of such inorganic acids include hydrochloric, hydrobromic, hydroiodic, nitric, carbonic, sulfuric and phosphoric acid. Appropriate organic acids can be selected from aliphatic, cycloaliphatic, aromatic, arylaliphatic, heterocyclic, carboxylic and sulfonic classes of organic acids.

Suitable base addition salts of the compounds disclosed herein can be prepared from a metallic salt or an organic salt. Metallic salts can be prepared from aluminum, calcium, lithium, magnesium, potassium, sodium and zinc. Organic salts can be prepared from N,N'-dibenzylethylene-diamine, chloroprocaine, choline, diethanolamine, ethylenediamine, N-methylglucamine, lysine, arginine, procaine, and any pharmaceutically acceptable organic bases.

The term "halogen atom" refers to a fluorine, chlorine, bromine or iodine atom.

The term "amino group" refers to an —NH$_2$ group. The term "amino group" also includes an amino group substituted with another atom or a group of atoms.

The term "alkyl group" refers to a linear or branched, saturated hydrocarbon based chain including 1 to 10 carbon atoms. The alkyl group can be a lower alkyl group including 1 to 4 carbon atoms. The term "alkyl group" also includes a substituted alkyl group.

The term "cycloalkyl group" refers to a cyclic saturated hydrocarbon based chain including 3 to 7 carbon atoms. The term "cycloalkyl group" also includes a substituted cycloalkyl group.

The term "alkenyl group" refers to a linear or branched unsaturated hydrocarbon based chain including 2 to 10 carbon atoms and including one or more double bonds. The term "alkenyl group" also includes a substituted alkenyl group.

The term "alkynyl group" refers to a linear or branched, and/or unsaturated hydrocarbon based chain including 2 to 10 carbon atoms and including one or more triple bonds. The term "alkynyl group" also includes a substituted alkynyl group.

The term "alkoxy group" refers to an oxygen atom substituted with an alkyl group.

The term "aryl group" refers to an aromatic hydrocarbon based ring or two fused aromatic hydrocarbon based rings. The aromatic hydrocarbon based ring can include 3 to 10 carbon atoms. Examples of aryl groups include phenyl and naphthyl groups. The term "aryl group" also includes a substituted aryl group.

The term "aralkyl group" refers to an alkyl substituted with an aryl group. The term "aralkyl group" also includes a substituted aralkyl group.

The term "heterocyclic group" refers to a saturated or unsaturated, cyclic or polycyclic hydrocarbon based chain including one or more heteroatoms chosen from O, S, and N. The hydrocarbon based chain can include 3 to 10 carbon atoms. The term "heterocyclic group" also includes a substituted heterocyclic group.

The term "heteroaryl group" refers to an aromatic heterocyclic group, such as a cyclic or polycyclic aromatic hydrocarbon based chain, including one or more heteroatoms chosen from O, S and N. Accordingly, a heteroaryl group is an example of a heterocyclic group. The aromatic hydrocarbon based chain can include 3 to 10 atoms and one or more double bonds. The polycyclic aromatic hydrocarbon based chain includes two or more fused aromatic rings. The term "heteroaryl group" also includes a substituted heteroaryl group.

The different "R" groups described above can be optionally substituted, for example, with a halogen atom, a hydroxyl group, an amino group, a —NH$_2$ group, a cyano group, a nitro, an alkyl group, an alkoxy group, an alkenyl group, an aryl group, a heterocyclic group, or a sulfonyl group. As an example, the "R" groups can be substituted with a methyl, a trifluoromethyl, an amide, a carbamate, a sulfonylamide, or a benzamide.

In particular embodiments, the R group of the drug of Formula (I) or (II) is —NHOH. In particular embodiments, the R group of the drug of Formula (II) is —NHOH and n is 6.

Many of the known HDACis contain a hydroxamic or benzamide zinc binding group (ZBG). It has been reported that inhibition of zinc dependent HDACs have great potential in cancer therapy. SAHA is an example of such a HDACi.

In particular embodiments, the current disclosure provides drugs of Formula (I) or (II), wherein the R group is a ZBG. Examples of ZBGs include hydroxamic acids, thiolhydroxamic acids, hydroxylamines, carboxylates, nitros, thiols, dithiols, mercaptoacetamides, trithiocarbonates, thioesters, benzamides, epoxides, epoxyketones, trifluoromethyl ketones, ketos, ketoamides, hydroxypyridinones, pyrones, hydroxylpyridinethiones, and thiopyrones (U.S. Pat. No. 9,139,565).

In particular embodiments, the ZBGs include

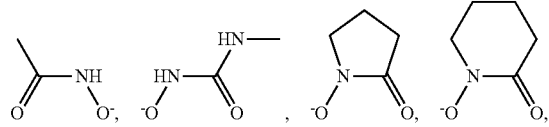

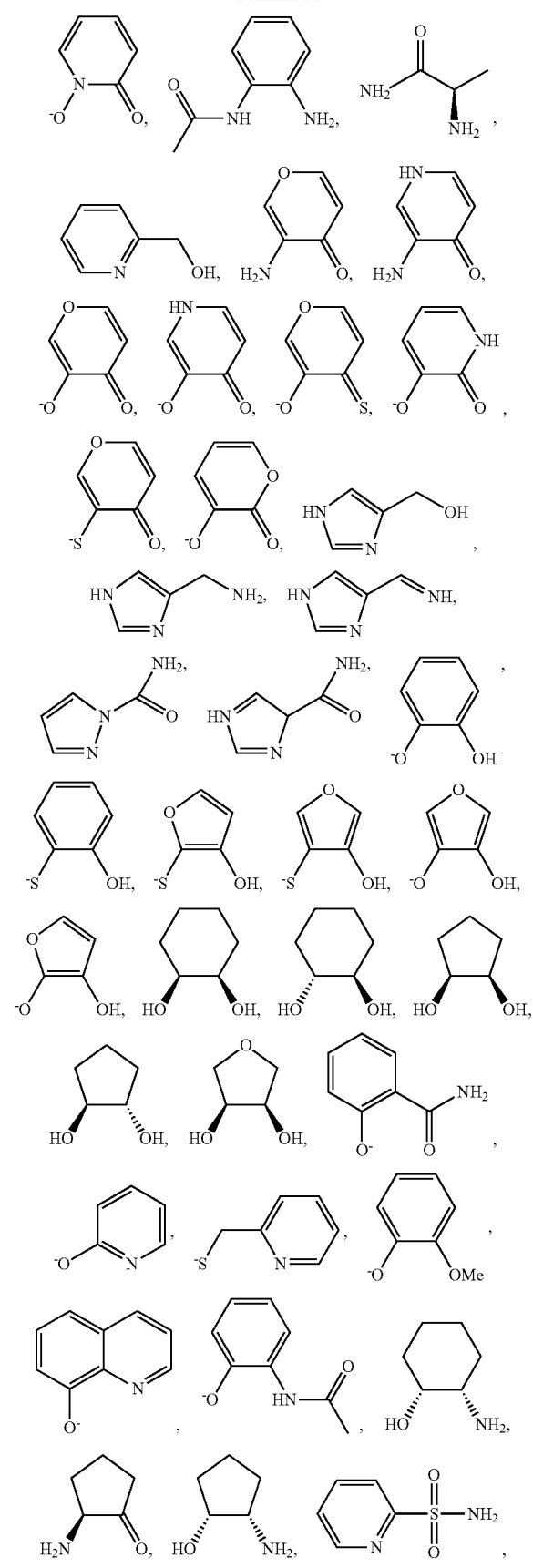

-continued

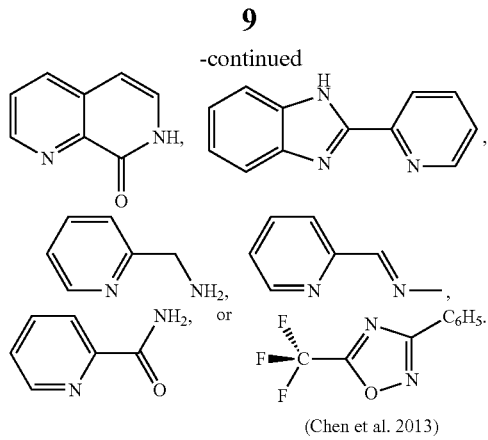

(Chen et al. 2013)

A ZBG can be covalently attached to a drug disclosed herein having Formula (I), (II), or (III) by known methods.

In particular embodiments, the current disclosure provides a drug of Formula (III), Formula (III)

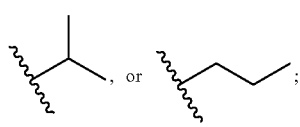

wherein:
n is 0 to 10;
A and B are independently, an aryl group or a heteroaryl group (as described above);
X is a $CH_2$ group, a CH group, a nitrogen atom, an oxygen atom, a sulfur atom, or a carbonyl group;
Y is a $CH_2$ group, a CH group, a nitrogen atom, an oxygen atom, a sulfur atom, or a carbonyl group;
----- is either present so as to form a double bond between X and Y, or is absent;
W is —$CF_3$, —$CHF_2$, —$CH_2F$, —$CH_3$, —$C_2H_6$,

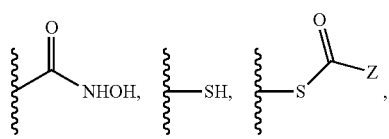

and
R is a ZBG.

In particular embodiments, in Formula (III), A and B are independently an aryl group or a heteroaryl group with 3 to 10 atoms in the aromatic ring. Moreover, in particular embodiments, in Formula (III), A and B independently, can be phenyls.

Further, in particular embodiments, in Formula (III), the ZBG is

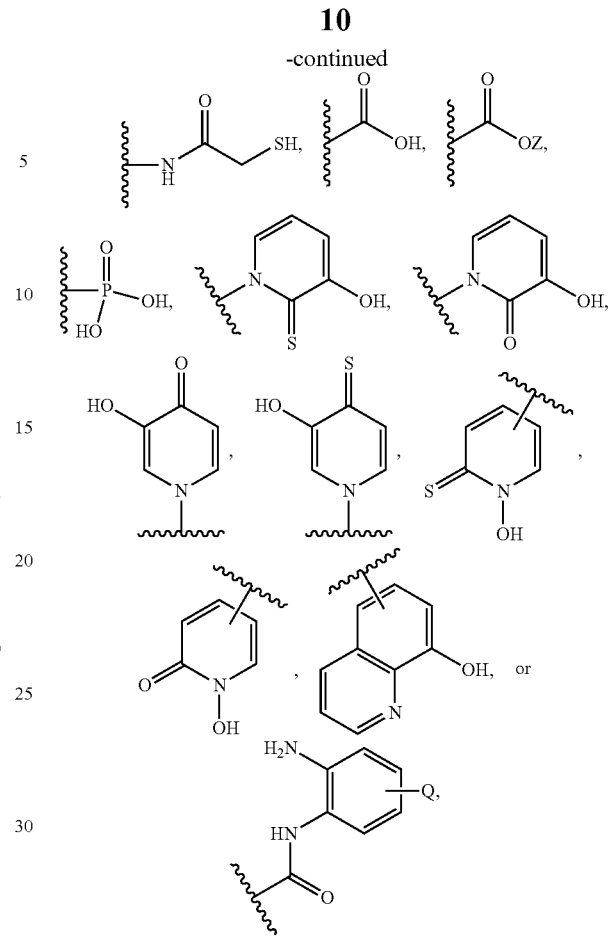

wherein:
Z is a alkyl group; and
Q is an alkyl group, a halogen atom, or an amino group.

The current disclosure provides compositions including a drug disclosed herein and a carrier. In particular embodiments, the composition is a pharmaceutical composition and the carrier is a pharmaceutically acceptable carrier.

The compositions described herein can be used to inhibit the growth of and/or kill AR-positive cancer cells including Enz-resistant cancer cells. The drugs described herein contain partial chemical scaffolds of Enz and SAHA, with weakened intrinsic pan-HDACi activities, which enables it to more selectively target and physically disrupt AR and critical proteins associated with AR, including Hsp90 and other proteins, in Enz-resistant PCa cells. It was shown that the exemplary compounds disclosed herein not only inhibited the growth of but also caused cell death to (killed) Enz-resistant PCa cells (see FIGS. 6A-6D). The inhibitory activity of the exemplary compounds were comparable, if not better than, SAHA.

Moreover, the compositions described herein are useful in degrading the full length AR and in degrading other critical proteins such as Hsp90 by utilizing AR as a vehicle. It was shown that in contrast to Enz, the exemplary compounds disclosed herein were able to degrade the full length AR and Hsp90 in Enz-resistant PCa cells that expressed the full length AR. In Enz-resistant PCa cells that express both the truncated and the full length AR for hormone-independent growth, the degradation of the full length AR resulted in loss of cell growth in hormone-depleted media (see FIG. 6D). Degradation of a protein includes breaking down the protein resulting in loss of function. The term degradation also includes truncating a protein. As an example, the full length AR protein may be truncated and can no longer bind to its ligand.

The methods disclosed herein can be used to treat subjects (humans, veterinary animals (dogs, cats, reptiles, birds, etc.) livestock (horses, cattle, goats, pigs, chickens, etc.) and research animals (monkeys, rats, mice, fish, etc.). Subjects in need of a treatment (in need thereof) are subjects diagnosed with AR positive cancer including prostate cancer such as CRPC, and breast cancer.

Treating subjects includes delivering therapeutically effective amounts of the compositions disclosed herein. Therapeutically effective amounts of the compositions disclosed herein have an anti-cancer effect, particularly on AR positive cancer including prostate cancer and breast cancer. Cancer (medical term: malignant neoplasm) refers to a class of diseases in which a group of cells display uncontrolled growth (division beyond the normal limits), invasion (intrusion on and destruction of adjacent tissues), and sometimes metastasis. "Metastasis" refers to the spread of cancer cells from their original site of proliferation to another part of the body. For solid tumors, the formation of metastasis is a very complex process and depends on detachment of malignant cells from the primary tumor, invasion of the extracellular matrix, penetration of the endothelial basement membranes to enter the body cavity and vessels, and then, after being transported by the blood or lymph, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential.

A "tumor" is a swelling or lesion formed by an abnormal growth of cells (called neoplastic cells or tumor cells). A "tumor cell" is an abnormal cell that divides by a rapid, uncontrolled cellular proliferation and continues to divide after the stimuli that initiated the new division cease. Tumors show partial or complete lack of structural organization and functional coordination with the normal tissue, and usually form a distinct mass of tissue, which may be either benign, pre-malignant or malignant.

As used herein, an anti-cancer effect refers to a biological effect, which can be manifested by a decrease in tumor volume, a decrease in the number of cancer cells, a decrease in the number of metastases, an increase in life expectancy, or a decrease of various physiological symptoms associated with the cancerous condition. An anti-cancer effect can also be manifested by a decrease in recurrence or an increase in the time before recurrence.

Therapeutically effective amounts also include those that provide an effective amount. An "effective amount" is the amount of active agent(s) or composition(s) necessary to result in a desired physiological change in vivo or in vitro. Effective amounts are often administered for research purposes. Effective amounts disclosed herein have an anti-cancer effect which can be evidenced by an anti-solid tumor effect. In particular embodiments, effective amounts can be assessed using cell growth as determined by MTT and colony formation assays. Cell counting as a golden standard can be performed routinely to determine cell doubling times and growth rates. Cell viability can be determined by trypan blue exclusion and LDH release assays.

For administration, therapeutically effective amounts (also referred to herein as doses) can be initially estimated based on results from in vitro assays and/or animal model studies. Such information can be used to more accurately determine useful doses in subjects of interest. Particularly useful pre-clinical tests include measure of cell growth, cell death, and/or cell viability.

The actual dose amount administered to a particular subject can be determined by a physician, veterinarian, or researcher taking into account parameters such as physical, physiological and psychological factors including target, body weight, stage of cancer, the type of cancer, previous or concurrent therapeutic interventions, idiopathy of the subject, and route of administration.

Exemplary doses can include 0.05 mg/kg to 5.0 mg/kg of the drug disclosed herein. The total daily dose can be 0.05 mg/kg to 30.0 mg/kg of a drug administered to a subject one to three times a day, including administration of total daily doses of 0.05-3.0, 0.1-3.0, 0.5-3.0, 1.0-3.0, 1.5-3.0, 2.0-3.0, 2.5-3.0, and 0.5-3.0 mg/kg/day of administration forms of a drug using 60-minute oral, intravenous or other dosing. In one particular example, doses can be administered QD or BID to a subject with, e.g., total daily doses of 1.5 mg/kg, 3.0 mg/kg, or 4.0 mg/kg of a composition with up to 92-98% wt/v of the compounds disclosed herein.

Additional useful doses can often range from 0.1 to 5 µg/kg or from 0.5 to 1 µg/kg. In other examples, a dose can include 1 µg/kg, 5 µg/kg, 10 µg/kg, 20 µg/kg, 40 µg/kg, 80 µg/kg, 150 µg/kg, 200 µg/kg, 350 µg/kg, 500 µg/kg, 750 µg/kg, 1000 µg/kg, or from 0.1 to 5 mg/kg or from 0.5 to 1 mg/kg. In other examples, a dose can include 1 mg/kg, 5 mg/kg, 10 mg/kg, 20 mg/kg, 40 mg/kg, 80 mg/kg, 150 mg/kg, 500 mg/kg, 1000 mg/kg, or more.

Therapeutically effective amounts can be achieved by administering single or multiple doses during the course of a treatment regimen (e.g., hourly, every 2 hours, every 3 hours, every 4 hours, every 6 hours, every 9 hours, every 12 hours, every 18 hours, daily, every other day, every 3 days, every 4 days, every 5 days, every 6 days, weekly, every 2 weeks, every 3 weeks, or monthly).

In particular embodiments, the compositions disclosed herein can be used in conjunction with other cancer treatments. For example, the composition disclosed herein can be administered in combination with other active ingredients, for example, a gonadotropin-releasing hormone agonist or antagonist (e.g., Lupron, Zoladex (Goserelin), Degarelix, Ozarelix, ABT-620 (Elagolix), TAK-385 (Relugolix), EP-100 or KLH-2109); a phosphoinositide 3-kinase (PI3K) inhibitor, a TORC inhibitor, or a dual PI3K/TORC inhibitor (e.g., BEZ-235, BKM120, BGT226, BYL-719, GDC0068, GDC-0980, GDC0941, GDC0032, MK-2206, OSI-027, CC-223, AZD8055, SAR245408, SAR245409, PF04691502, WYE125132, GSK2126458, GSK-2636771, BAY806946, PF-05212384, SF1126, PX866, AMG319, ZSTK474, CaI101, PWT33597, LY-317615 (enzastaurin hydrochloride), CU-906, or CUDC-907); a CYP17 inhibitor in addition to Galeterone (e.g., abiraterone acetate (Zytiga), TAK-700 (orteronel), or VT-464); prednisone; an osteoprotective agent; a radiation therapy; a kinase inhibitor (e.g. MET, VEGFR, EGFR, MEK, SRC, AKT, RAF, FGFR, CDK4/6); Provenge, Prostvac, Ipilimumab, a PD-1 inhibitor; a taxane or tubulin inhibitor; an anti-STEAP-1 antibody; a heat shock protein 90 (HSP90) or heat shock protein 27 (HSP27) pathway modulator; an anti-androgen (e.g. bicalutamide); and/or immunotherapy.

As suggested, the drugs described herein can be formulated into compositions. Each drug can be formulated into its own composition for administration or the drug can be formulated with an additional active ingredient for administration as a composition. The drug described herein and the additional active ingredient can be used in a combination therapy.

The compositions described herein can be administered simultaneously or sequentially within a selected time window, such as within 10 minutes, 1 hour, 3 hour, 10 hour, 15 hour, 24 hour, or 48 hour time windows or when the complementary active ingredient is within a clinically-relevant therapeutic window.

For injection, compositions can be formulated as aqueous solutions, such as in buffers including Hanks' solution, Ringer's solution, or physiological saline. The aqueous solutions can contain formulatory agents such as suspending, stabilizing, and/or dispersing agents. Examples of suitable aqueous and non-aqueous carriers, which may be employed in the injectable formulations include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of selected particle size in the case of dispersions, and by the use of surfactants.

Injectable formulations may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like in the compositions.

Alternatively, the composition can be in lyophilized form and/or provided in powder form for constitution with a suitable vehicle, e.g., sterile pyrogen-free water, before use. Lyophilized compositions can include less than 5% water content; less than 4.0% water content; or less than 3.5% water content.

In particular embodiments, the composition can be in a unit dosage form, such as in a suitable diluent in sterile, hermetically sealed ampoules or sterile syringes.

In particular embodiments, in order to prolong the effect of a composition, it is desirable to slow the absorption of the active ingredient(s) following injection. Compositions can be formulated as sustained-release systems utilizing semipermeable matrices of solid polymers containing at least one administration form. Various sustained-release materials have been established and are well known by those of ordinary skill in the art. Sustained-release systems may, depending on their chemical nature, release active ingredients following administration for a few weeks up to over 100 days.

In particular embodiments, delayed absorption can be accomplished by dissolving or suspending the active ingredient(s) in an oil vehicle. In particular embodiments, administration forms can be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salts. In addition, prolonged absorption of the injectable composition may be brought about by the inclusion of agents which delay absorption such as aluminum monostearate and gelatin.

Injectable depot forms can be made by forming microencapsule matrices of administration forms in biodegradable polymers such as polylactide-polyglycolide. Depending on the ratio of administration form to polymer, and the nature of the particular polymer employed, the rate of administration form release can be controlled. Examples of other biodegradable polymers include poly(orthoesters) and poly (anhydrides). Injectable depot formulations are also prepared by entrapping the active ingredient(s) in liposomes or microemulsions which are compatible with body tissue.

Alternatively, delayed absorption of a composition can be accomplished by the use of a liquid suspension of crystalline or amorphous material having poor water solubility. The rate of absorption of the active ingredient(s) then depends upon its rate of dissolution which, in turn, may depend upon crystal size and crystalline form.

Compositions can also be administered with anesthetics including ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and/or phenazopyridine.

Compositions can also be formulated for oral administration. For ingestion, compositions can take the form of tablets, pills, lozenges, sprays, liquids, and capsules formulated in conventional manners. Ingestible compositions can be prepared using conventional methods and materials known in the pharmaceutical art. For example, U.S. Pat. Nos. 5,215,754 and 4,374,082 relate to methods for preparing swallowable compositions. U.S. Pat. No. 6,495,177 relates to methods to prepare chewable supplements with improved mouthfeel. U.S. Pat. No. 5,965,162, relates to compositions and methods for preparing comestible units which disintegrate quickly in the mouth.

Ingestible compositions may have a shape containing no sharp edges and a smooth, uniform and substantially bubble free outer coating. Coatings of ingestible compositions can be derived from a polymeric film. Such film coatings reduce the adhesion of the compositions to the inner surface of the mouth and can aid in masking potential unpleasant tastes. Coatings can also protect the compositions from atmospheric degradation. Exemplary polymeric films include vinyl polymers, cellulosics, acrylates and methacrylates, natural gums and resins such as zein, gelatin, shellac and acacia. Other common excipients used in ingestible compositions include sucrose, fructose, lactose, glucose, lycasin, xylitol, lactitol, erythritol, mannitol, isomaltose, dextrose, polydextrose, dextrin, compressible cellulose, compressible honey, compressible molasses, fondant or gums, vegetable oils, animal oils, alkyl polysiloxanes, corn starch, potato starch, pre-gelatinized starches, stearic acid, calcium stearate, magnesium stearate, zinc stearate, benzoic acid, and colorants For administration by inhalation (e.g., nasal or pulmonary), the compositions can be formulated as aerosol sprays for pressurized packs or a nebulizer, with the use of suitable propellants, e.g. dichlorodifluoromethane, trichlorofluoromethane, or dichlorotetra-fluoroethane.

As suggested, nanoparticle formulations for a variety of administration routes can also be used.

Any composition described herein can advantageously include any other pharmaceutically acceptable carriers which include those that do not produce significantly adverse, allergic, or other untoward reactions that outweigh the benefit of administration, whether for research, prophylactic, and/or therapeutic treatments. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety, and purity standards as required by U.S. FDA Office of Biological Standards and/or other relevant foreign regulatory agencies.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants. Fillers and excipients are commercially available from companies such as Aldrich Chemical Co., FMC Corp, Bayer, BASF, Alexi Fres, Witco, Mallinckrodt, Rhodia, ISP, and others.

In particular embodiments, the compositions can include, for example, 0.5 µg/mL or mg/mL or mg, 1 µg/mL or mg/mL or mg, 10 µg/mL or mg/mL or mg, 25 µg/mL or mg/mL or mg, 50 µg/mL or mg/mL or mg, 100 µg/mL or mg/mL or mg, 200 µg/mL or mg/mL or mg, 400 µg/mL or mg/mL or mg, 800 µg/mL or mg/mL or mg, or more of one or more of the active ingredients.

The present disclosure further provides for kits including one or more treatment options for practicing any of the methods described herein. The kits may include a notice in the form prescribed by a governmental agency regulating the manufacture, use or sale of pharmaceuticals, biological products, lab developed tests, etc., which notice reflects approval by the agency of the manufacture, use or sale for human administration and/or testing. Treatment portions of the kits may include a drug described herein in a ready-to-use form and/or a form that requires preparation before administration (e.g., lyophilized). The kits may also include syringes, pipettes, antiseptics, tubing, gloves, diluents, etc. as well as instructions for practicing any method described herein which may include relevant reference levels.

The Exemplary Embodiments and Example below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

EXEMPLARY EMBODIMENTS

1. A drug of Formula (I) or Formula (II),

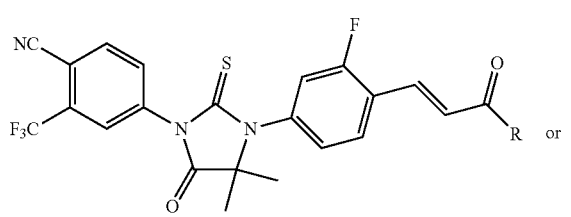

Formula (I)

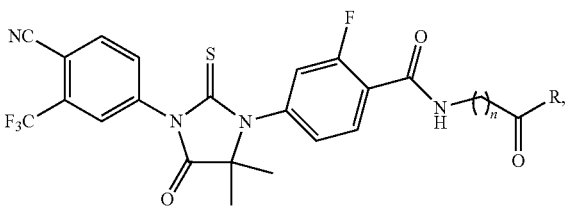

Formula (II)

wherein:
n is 1 to 10; and
R is a hydrogen atom, a halogen atom, a hydroxyl group, a nitro group, an amino group, an alkyl group, a cycloalkyl group, an alkenyl group, an alkynyl group, an alkoxy group, an aryl group, an aralkyl group, or a heterocyclic group.

2. The drug of Formula (I) or Formula (II) of embodiment 1, wherein R is —NHOH.

3. The drug of embodiment 1 or 2, wherein the drug has Formula (II) and wherein n is 6 and R is —NHOH.

4. A drug of Formula (III),

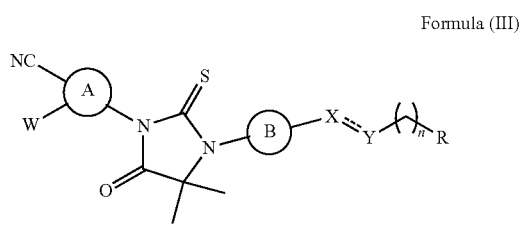

Formula (III)

wherein:
n is 0 to 10;
A and B are independently, an aryl group or a heteroaryl group;
X is a CH$_2$ group, a CH group, a nitrogen atom, an oxygen atom, a sulfur atom, or a carbonyl group;
Y is a CH$_2$ group, CH group, a nitrogen atom, an oxygen atom, a sulfur atom, or a carbonyl group;
----- is either present so as to form a double bond, or is absent;
W is —CF$_3$, —CHF$_2$, —CH$_2$F, —CH$_3$, —C$_2$H$_6$,

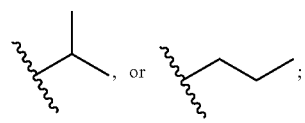

, or

;

and
R is a zinc binding group (ZBG).

5. The drug of embodiment 4, wherein the ZBG is

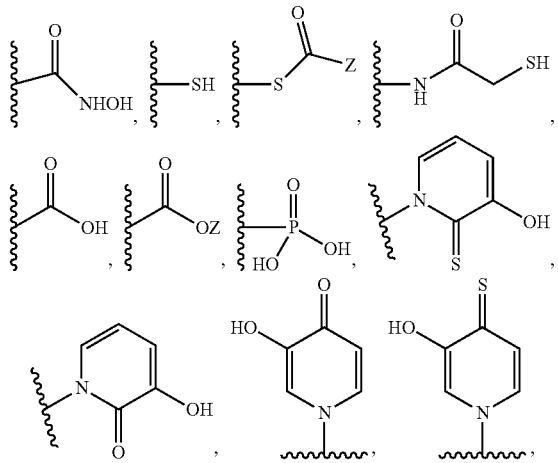

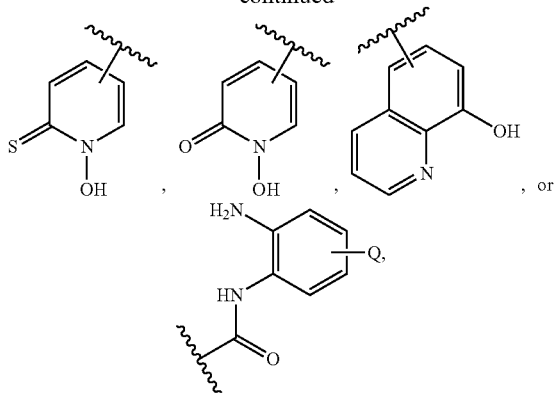

wherein:

Z is a alkyl group; and

Q is an alkyl group, a halogen atom, or an amino group.

6. The drug of embodiment 4 or 5, wherein A and B have 3 to 10 atoms in the aromatic ring.

7. The drug of any one of embodiments 4-6, wherein A and B are independently phenyls.

8. A composition including the drug of any one of embodiments 1-7 and a carrier.

9. A pharmaceutical composition including the drug of any one of embodiments 1-7 and a pharmaceutically acceptable carrier.

10. A method of providing an anti-cancer effect in a subject having androgen receptor (AR) positive cancer, wherein the method includes administering a therapeutically effective amount of the composition of embodiment 8 or 9 to the subject, thereby providing an anti-cancer effect in the subject.

11. A method of treating AR positive cancer in a subject in need thereof, wherein the method includes administering a therapeutically effective amount of the composition of embodiment 8 or 9 to the subject in need thereof, thereby treating the AR positive cancer.

12. The method of embodiment 10 or 11, wherein the AR positive cancer is prostate cancer or breast cancer.

13. The method of embodiment 10 or 11, wherein the prostate cancer is castration-resistant prostate cancer (CRPC).

14. The method of any one of embodiments 10-13, wherein the composition includes a second active ingredient.

15. The method of any one of embodiments 10-13, wherein the composition is administered in conjunction with a second composition including an active ingredient.

16. The method of embodiment 15, wherein the composition of embodiment 8 or 9 and the second composition are administered simultaneously.

17. The method of embodiment 15, wherein the composition of embodiment 8 or 9 and the second composition are administered sequentially.

18. A method of inhibiting growth of AR positive cancer cells, wherein the method includes contacting AR positive cancer cells with an effective amount of the composition of embodiment 8 or 9.

19. A method of killing AR positive cancer cells, wherein the method includes contacting AR positive cancer cells with an effective amount of the composition of embodiment 8 or 9.

20. A method of degrading a full length androgen receptor (AR) and degrading or disrupting other critical proteins such as Hsp90 and other Hsp90 client proteins in a manner that is dependent on AR, wherein the method includes contacting AR positive cancer cells expressing the full length AR with an effective amount of the composition of embodiment 8 or 9.

Example 1. Background

An attractive strategy to attenuate AR signaling and to overcome resistance to androgen depletion is to induce destabilization and degradation of the AR protein in CRPC cells. AR is stabilized in the cytosol by its interaction with heat shock protein 90 (Hsp90) and other chaperone proteins. Hsp90 is commonly overexpressed in many types of cancer cells and is being actively explored as a drug target for cancer treatment, including PCa (Bhat et al., 2014; Neckers and Workman, 2012). Hsp90 is an ATP-dependent molecular chaperone that aids the folding and stability of a number of client proteins, such as steroid receptors, protein kinases, transcription factors and proteins involved in apoptosis. Therefore, inhibition of Hsp90 leads to degradation of its client proteins via the ubiquitin-proteasome pathway. Association of the AR apo-protein with Hsp90 is critical for stabilizing AR in a conformation that allows androgen binding (Fang et al., 1996; Veldscholte et al., 1992). In PCa cells, Hsp90 inhibitors induce AR degradation and impair AR nuclear translocation, simultaneously reducing the levels of other oncogenic client proteins, such as p-AKT/AKT, EGFR and IGF-IR and survivin (He et al., 2013; Liu et al., 2015; Saporita et al., 2007; Solit et al., 2002). Simultaneous disruption of AR and other aberrant growth/survival networks via Hsp90 inhibition is an advantageous treatment strategy for CRPC as this would silence potentially mutually compensatory oncogenic signaling pathways. Despite this attractive scientific rationale, clinical development of Hsp90 inhibitors for PCa treatment were disappointing (Heath et al., 2008; Oh et al., 2011; Pacey et al., 2011; Thakur et al., 2015) as it was limited by adverse toxicity profiles and induction of pro-survival heat shock response (Liu et al., 2015). Agents that more narrowly target Hsp90 interactions with specific client proteins in only cells that produce high levels of AR may overcome these limitations, enabling administration of effective and extended drug dosage regimens.

One of the actions of histone deacetylase (HDAC) inhibitors (HDACi) is to disrupt Hsp90 activity. HDACs remove acetyl groups from lysine residues of histone and non-histone proteins. Eighteen HDACs categorized into four classes have been identified in mammalian cells. Among them, HDAC6 is a zinc-dependent, class-IIb HDAC and is localized in the cytoplasm (Kramer et al., 2014). HDAC6 deacetylates Hsp90 (Bali et al., 2005; Kovacs et al., 2005). Inhibition of HDAC6 could result in hyper-acetylation of Hsp90, loss of ATP binding and dissociation and degradation of its client proteins, including AR. The HDACi LAQ-824 (Chen et al., 2005), PDX-101 (i.e. Belinostat) (Gravina et al., 2013), suberoylanilide hydroxamic acid (SAHA or vorinostat) (Marrocco et al., 2007; Sato et al., 2012) and natural products sulforaphane (Gibbs et al., 2009) and genistein (Basak et al., 2008) have all been reported to reduce AR protein levels in PCa cells by disrupting the HDAC6-Hsp90 chaperone function.

Although nuclear HDACs (e.g., HDAC1 and HDAC3) are indispensable for AR transcriptional activity (Welsbie et al., 2009) and increased HDAC levels have been reported in clinical CRPC samples and positively correlated to Gleason scores (Burdelski et al., 2015; Weichert et al., 2008), they are not likely to serve as effective drug targets to treat PCa by using currently available HDACi. Indeed, clinical use of HDACi is now confined to hematological malignancies. A few HDACi, such as vorinostat (SAHA) (Bradley et al., 2009), romidepsin (FK-228) (Molife et al., 2010), panobinostat (LBH-589) (Rathkopf et al., 2013) and pracinostat (SB-939) (Eigl et al., 2015) have been tested in CRPC patients. However, they suffered constraints of dose-limiting toxicity that prevented further dose escalation and long-term treatment, resulting in modest outcomes. Moreover, recent studies have associated the pleiotropic effects of HDACi, particularly epigenetic modifications of chromatin-associated proteins, with induction of epithelial to mesenchymal transition (EMT) in prostate, endometrial and nasopharyngeal cancer cells (Jiang et al., 2013; Kong et al., 2012; Tam and Weinberg, 2013; Uchida et al., 2012). Therefore clinical translation of the extensive and promising pre-clinical findings of the efficacies of HDACi in treating solid tumors must address the issue of toxicities that prevent application of effective HDACi treatment regimens in the clinic.

It was sought to develop compounds that would effectively antagonize AR signaling in CRPC cells while avoiding the drug resistance or toxicities encountered with Enz, HDACi and Hsp90 inhibitors. The approach was to design new molecules that incorporated modified functional moieties of Enz and HDACi. Accordingly, prototype compounds 2-75 and 1005 were designed, synthesized, and tested. The 2-75 and 1005 chemical scaffolds were designed to retain AR binding affinity which would allow targeting of HDACi activity to the AR-Hsp90-HDAC6 complex in the cytosol. The compounds were also designed to have lower intrinsic HDACi activity compared to SAHA, thus reducing the HDACi activity against non-target proteins, both in the nucleus and in the cytosol. Nevertheless, targeting of the HDACi activity through AR was expected to cause disruption of the AR signaling axis and also other Hsp90 interactions and growth inhibition or loss of viability in Enz-resistant CRPC cells. This would enable the use of effective and extended drug dosage regimens in contrast to currently available HDACi drugs.

Example 1. Synthesis of Compounds 2-75, 1005, 3-52 and 1002

(E)-ethyl-3-(4-(3-(4-cyano-3-(trifluoromethyl)phenyl)-5,5-dimethyl-4-oxo-2-thioxoimidazolidin-1-yl)-2-fluorophenyl)acrylate 2 (1002). Compound 1 (420 mg, 0.78 mmol), Pd(OAc)2 (8.7 mg, 0.04 mmol) and P(o-tolyl)3 (24 mg, 0.08 mmol) were mixed in a flask. DMF (6 ml) and DI PEA (2 ml) were added via syringe under argon followed by the addition of ethyl acrylate (0.1 mL, 1 mmol). The reaction mixture was heated at 80° C. for 5 h. After cooling to ambient temperature, the reaction mixture was diluted with EtOAc and washed with water and brine, dried over Na2SO4. Purification by silica gel column (Hexane/EtOAc=4/1) provided the title compound (297 mg, 75%) as slightly brown powder. 1H NMR (400 MHz, CDCl3): δ 7.99-7.96 (m, 2H), 7.85-7.79 (m, 2H), 7.70 (t, J=8.2 Hz, 1H), 7.17-7.11 (m, 2H), 6.61 (d, J=16.4 Hz, 1H), 4.29 (q, J=7.2 Hz, 2H), 1.62 (s, 6H), 1.36 (t, J=7.2 Hz, 3H). 13C NMR (100 MHz, CDCl3): δ 179.74, 174.48, 166.28, 161.14 (d, J=255.5 Hz), 137.36 (d, J=10.2 Hz), 136.86, 135.51 (d, J=1.0 Hz), 135.24, 133.59 (q, J=33.3 Hz), 132.12, 129.98 (d, J=4.0 Hz), 127.03 (q, J=4.7 Hz), 125.86 (d, J=3.7 Hz), 123.16, 122.85 (d, J=6.5 Hz), 120.44, 117.91 (d, J=23.6 Hz), 114.68, 110.31 (d, J=2.0 Hz), 66.57, 60.88, 23.76, 14.21.

(E)-3-(4-(3-(4-cyano-3-(trifluoromethyl)phenyl)-5,5-dimethyl-4-oxo-2-thioxoimidazolidin-1-yl)-2-fluorophenyl) acrylic acid (3). Compound 1002 (297 mg, 0.58 mmol) was dissolved in a mixture of acetonitrile (7 mL) and HCl (37%, 2 mL). The reaction mixture was refluxed until the completion shown by TLC. After the solvent was removed under reduced pressure, the residue was partitioned between EtOAc and water. The collected organic phase was washed with water and brine, dried over Na$_2$SO$_4$. Purification by silica gel column (Hexane/EtOAc/AcOH=3/2/0.5%) provided the title compound (257 mg, 91%) as white foam solid. $^1$H NMR (400 MHz, Acetone-d$_6$): δ 8.28 (d, J=8.0 Hz, 1H), 8.20 (d, J=1.6 Hz, 1H), 8.08 (dd, J=8.4 Hz, 2.0 Hz, 1H), 8.01 (t, J=8.4 Hz, 1H), 7.83 (d, J=16 Hz, 1H), 7.42-7.37 (m, 2H), 6.71 (d, J=16 Hz, 1H), 1.68 (s, 6H). $^{13}$C NMR (100 MHz, Acetone-d$_6$): δ 181.38, 175.66, 167.21, 161.77 (d, J=251.8 Hz), 139.59 (d, J=10.6 Hz), 139.03, 136.66, 136.29 (d, J=3.1 Hz), 134.28, 132.89 (q, J=32.7 Hz), 130.69 (d, J=3.9 Hz), 128.50 (q, J=4.9 Hz), 127.52 (d, J=3.5 Hz), 124.66, 124.23 (d, J=11.6 Hz), 123.34 (d, J=5.8 Hz), 118.96 (d, J=23.6 Hz), 115.62, 110.29, 67.63, 23.65. LR-MS for C$_{22}$H$_{15}$F$_4$N$_3$O$_3$S [M−H]$^-$ Calcd 476.1. found 476.2.

(E)-3-(4-(3-(4-cyano-3-(trifluoromethyl)phenyl)-5,5-dimethyl-4-oxo-2-thioxoimidazolidin-1-yl)-2-fluorophenyl)-N-((tetrahydro-2H-pyran-2-yl)oxy)acrylamide (4). A flask was charged with compound 13 (90 mg, 0.19 mmol), NH2OTHP (24 mg, 0.21 mmol) and BOP (93 mg, 0.21 mmol), then filled with argon, DMF (2 mL) and DIPEA (65 μL, 0.38 mmol) were added using syringe. The reaction mixture was stirred overnight at ambient temperature and quenched by adding water. Product was extracted with EtOAc and washed with water and brine, dried over Na2SO4. Purification by silica gel column (DCM/EtOAc=4/1) provided the title compound (55 mg, 51%) as white solid. 1H NMR (400 MHz, DMSO-d$_6$): δ 11.44 (s, 1H), 8.41 (d, J=8.4 Hz, 1H), 8.30 (s, 1H), 8.10 (d, J=8.4 Hz, 1H), 7.88 (t, 1H), 7.60 (d, J=16 Hz, 1H), 7.44 (m, 1H), 7.34 (d, J=8.0 Hz, 1H), 6.73 (d, J=16 Hz, 1H), 4.95 (bs, 1H), 4.01 (t, J=8.4 Hz, 1H), 3.56 (m, 1H), 1.72 (bs, 3H), 1.56 (bs, 9H).

(E)-3-(4-(3-(4-cyano-3-(trifluoromethyl)phenyl)-5,5-dimethyl-4-oxo-2-thioxoimidazolidin-1-yl)-2-fluorophenyl)-N-hydroxyacrylamide (1005). Compound 4 (35 mg, 0.06 mmol) was dissolved in MeOH (2 mL) and cooled in an ice bath. HCl (4N in dioxane, 0.3 mL) was added. The reaction was stirred at 0-4° C. for 1 h and evaporated to dryness. The residue was washed with cold ether and the product was obtained as white solid (18 mg, 60%). 1H NMR (400 MHz, MeOH-d4): δ 8.15-8.13 (m, 2H), 7.98 (d, J=8.0 Hz, 1H), 8.01 (t, J=8.0 Hz, 1H), 7.72 (d, J=16.0 Hz, 1H), 7.33-7.27 (m, 2H), 6.67 (d, J=16.0 Hz, 1H), 1.58 (s, 6H). LR-MS for C22H16F4N4O3S [M+H]+ Calcd 492.10. found 493.20.

4-(3-(4-cyano-3-(trifluoromethyl)phenyl)-5,5-dimethyl-4-oxo-2-thioxoimidazolidin-1-yl)-2-fluorobenzoic acid (5). HCOOLi (161 mg, 3.09 mmol), Ac2O (0.2 mL, 2.06 mmol) and DIPEA (0.36 mL, 2.06 mmol) were mixed in DMF (1 mL) and this mixture was stirred at ambient temperature for 1 h. Then, LiCl (129 mg, 3.09 mmol), Pd$_2$(dba)$_3$ (24 mg, 0.025 mmol) and compound 11 (550 mg, 1.03 mmol, dissolved in 1 mL DMF) were added. The reaction mixture was stirred at 80° C. overnight. After cooling to ambient temperature, the reaction was diluted with EtOAc, washed with 2M HCl, water, and brine, and dried over Na$_2$SO$_4$. Purification by silica gel column (Hexane/EtOAc/AcOH=3/2/0.5%) provided the title compound (430 mg, 92%) as off-white solid. $^1$H NMR (600 MHz, CDCl$_3$): δ 8.21 (t, J=8.4 Hz, 1H), 7.99 (d, J=8.4 Hz, 1H), 7.94 (s, 1H), 7.82 (dd, J=8.4 Hz, 1.8 Hz, 1H), 7.23 (dd, J=9.0 Hz, 1.8 Hz, 1H), 7.20 (dd, J=10.2 Hz, 1.8 Hz, 1H), 1.63 (s, 6H). $^{13}$C NMR (150 MHz, CDCl3): δ 179.63, 174.36, 167.43, 162.65 (d, J=264

Hz), 141.19 (d, J=9.8 Hz), 136.72, 135.33, 133.96, 133.71 (q, J=33 Hz), 132.11, 127.03 (q, J=4.5 Hz), 125.20 (d, J=3.4 Hz), 121.78 (q, J=273 Hz), 119.09, 118.93, 114.68, 110.46.

4-(3-(4-cyano-3-(trifluoromethyl)phenyl)-5,5-dimethyl-4-oxo-2-thioxoimidazolidin-1-yl)-2-fluoro-N-(7-oxo-7-(((tetrahydro-2H-pyran-2-yl)oxy)amino)heptyl)benzamide (6). A flask was charged with compound 5 (67 mg, 0.15 mmol), 7-amino-N-(tetrahydro-2H-pyran-2-yl)oxy heptanamide (74 mg, 0.3 mmol) and HBTU (86 mg, 0.225 mmol), then filled with argon, DMF (2 mL) and DIPEA (0.053 ml, 0.3 mmol)) were added via syringe. The reaction mixture was stirred overnight at room temperature and quenched by adding water. Product was extracted with EtOAc, washed with water and brine, and dried over $Na_2SO_4$. Purification by silica gel column (DCM/MeOH=20/1) provided the title compound (30 mg, 30%) as yellow oil. 1H NMR (600 MHz, CDCl3): δ 9.00 (bs, 1H), 8.18 (t, J=8.4 Hz, 1H), 7.94 (s, 1H), 7.91 (s, 1H), 7.79 (dd, J=8.4 Hz, 1.8 Hz, 1H), 7.19 (dd, J=8.4 Hz, 1.8 Hz, 1H), 7.11 (dd, J=10.8 Hz, 1.8 Hz, 1H), 6.81-6.73 (m, 1H), 4.95-4.88 (m, 1H), 3.97-3.86 (m, 1H), 3.60-3.53 (m, 1H), 3.49-3.41 (m, 2H), 2.13-2.04 (m, 2H), 1.85-1.70 (m, 4H), 1.67-1.47 (m, 6H), 1.57 (s, 6H), 1.41-1.31 (m, 4H).

4-(3-(4-cyano-3-(trifluoromethyl)phenyl)-5,5-dimethyl-4-oxo-2-thioxoimidazolidin-1-yl)-2-fluoro-N-(7-(hydroxyamino)-7-oxoheptyl)benzamide (2-75). Compound 6 (26 mg, 0.038 mmol) was dissolved in MeOH (2 mL) and cooled in an ice bath, HCl (4N in dioxane, 0.1 mL) was added. The reaction was stirred at 0-4° C. for 1 h and evaporated to dryness. Purification by silica gel column (DCM/MeOH=20/1) provided the title compound (7 mg, 32%) as brown solid. 1H NMR (600 MHz, CDCl3): δ 8.26-8.17 (m, 1H), 7.99 (d, J=8.4 Hz, 1H), 7.95 (s, 1H), 7.82 (d, J=8.4 Hz, 1H), 7.26-7.24 (m, 1H), 7.15 (d, J=11.4 Hz, 1H), 6.80 (s, 1H), 3.52-3.41 (m, 2H), 2.23-2.09 (m, 2H), 1.75-1.62 (m, 4H), 1.61 (s, 6H), 1.44-1.32 (m, 4H). 13C NMR (150 MHz, CDCl3): δ 179.77, 174.40, 171.20, 162.36, 160.31 (d, J=250 Hz), 139.03 (d, J=10.2 Hz), 136.76, 135.32, 133.67 (q, J=33.8 Hz), 133.27, 132.12, 127.05 (q, J=4.5 Hz), 126.22, 122.71, 121.84 (q, J=286 Hz), 117.97 (d, J=25.6 Hz), 114.68, 110.42, 66.64, 39.83, 32.50, 29.09, 28.08, 26.06, 24.92, 23.83. HR-ESI-MS m/z Calcd for C27H28F4N5O4S [M+H]+ 594.1798. found 594.1777.

Methyl-7-(4-(3-(4-cyano-3-(trifluoromethyl)phenyl)-5,5-dimethyl-4-oxo-2-thioxoimidazolidin-1-yl)-2-fluorobenzamido)heptanoate 7(3-52). A flask was charged with compound 17 (130 mg, 0.29 mmol), methyl 7-aminoheptanoate hydrochloride (86 mg, 0.44 mmol) and HBTU (167 mg, 0.44 mmol), then filled with argon, DMF (3 mL) and DIPEA (0.15 mL, 0.87 mmol)) were added via syringe. The reaction mixture was stirred overnight at room temperature and quenched by adding water. Product was extracted with EtOAc, washed with water and brine, and dried over $Na_2SO_4$. Purification by silica gel column (Hexane/EtOAc=2/1) provided the title compound (80 mg, 47%) as yellow oil. $^1$H NMR (600 MHz, CDCl$_3$): δ 8.24 (t, J=8.4 Hz, 1H), 7.97 (d, J=8.4 Hz, 1H), 7.94-7.92 (m, 1H), 7.81 (dd, J=8.4 Hz, 1.8 Hz, 1H), 7.22 (dd, J=8.4 Hz, 1.8 Hz, 1H), 7.13 (dd, J=11.4 Hz, 1.8 Hz, 1H), 6.71-6.66 (m, 1H), 3.65 (s, 3H), 3.51-3.45 (m, 2H), 2.30 (t, J=7.8 Hz, 2H), 1.67-1.61 (m, 4H), 1.60 (s, 6H), 1.43-1.33 (m, 4H). $^{13}$C NMR (150 MHz, CDCl3): δ 179.72, 174.42, 174.14, 161.95, 160.34 (d, J=248 Hz), 138.90 (d, J=10.8 Hz), 136.78, 135.29, 133.66 (q, J=33.3 Hz), 133.38 (d, J=3.4 Hz), 132.11, 127.04 (q, J=4.5 Hz), 126.15 (d, J=3.0 Hz), 122.90 (d, J=12.1 Hz), 121.79 (q, J=273 Hz), 117.89 (d, J=26.1 Hz), 114.69, 110.39, 66.60, 51.50, 40.09, 33.91, 29.23, 28.70, 26.54, 24.75, 23.82. HR-ESI-MS m/z Calcd for C28H29F4N4O4S [M+H]+ 593.1846. found 593.1829.

Figure 1A:
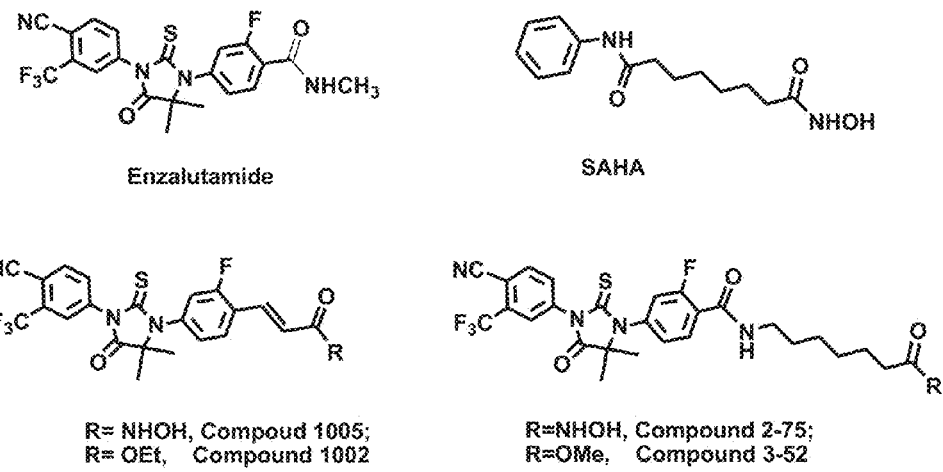
FIGS. 1A and 1B provide exemplary novel compounds and synthetic schemes. (1A) Chemical structures of Enz, SAHA, and Compounds 1005, 2-75, 1002 and 3-52. (1B) Synthesis of Compounds 1005, 2-75, 1002 and 3-52. Reagents and conditions: (a) ethyl acrylate, Pd(OAc)$_2$, P(o-tolyl)$_3$, DIPEA, DMF, 80° C., 75%; (b) 37% HCl (aq), acetonitrile, reflux, 91%; (c) NH$_2$OTHP, BOP, DIPEA, DMF, 51%; (d) HCl (4N in dioxane), MeOH, 60% for 1005, 32% for 2-75; (e) HCOOLi, Ac$_2$O, Pd$_2$(dba)$_3$, LiCl, DMF, 80° C., 92%; (f) 7-amino-N-(tetrahydro-2H-pyran-2-yl)oxy heptanamide, HBTU, DIPEA, DMF, 30%; (g) methyl 7-aminoheptanoate hydrochloride, HBTU, DIPEA, DMF, 47%.
Figure 1B:
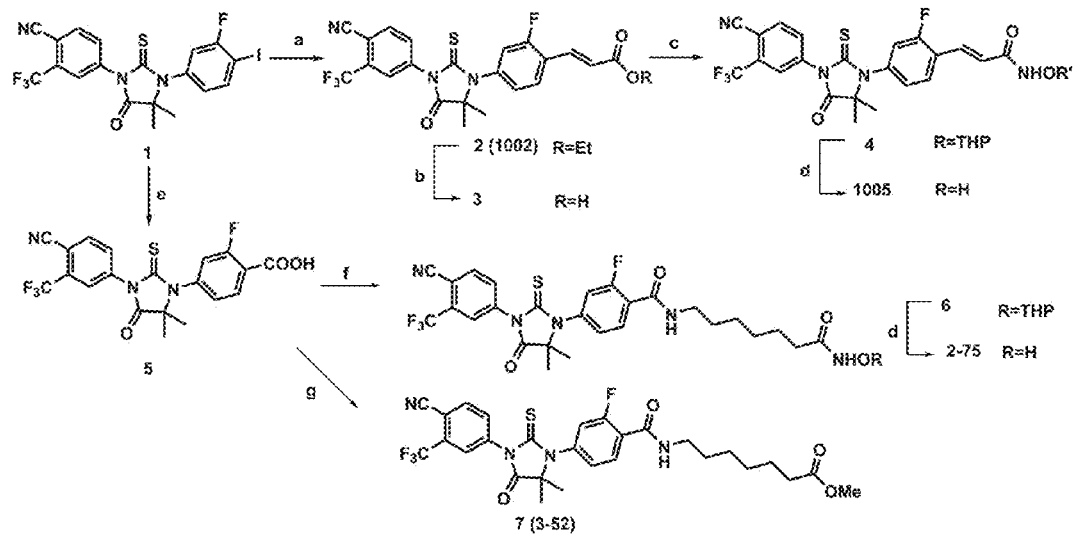

Design and synthesis of compounds 2-75 and 1005 with partial chemical scaffolds of Enz and SAHA. Compounds 2-75 and 1005 were designed to retain partial functional scaffolds of Enz and SAHA (FIG. 1A). Upon binding to AR, the cyano group of Enz/Enz derivatives forms a critical hydrogen bond with Arg752, and the conformationally restricted thiohydantoin ring in the middle forces the rest of the molecule to the "H11 pocket", a region near the C terminus of helix 11 and the loop connecting helices 11 and 12 (Balbas et al., 2013). To design derivatives with both AR-binding and HDACi activities, different linkers connecting Enz and a zinc binding group (ZBG) were introduced to retain the above structural features that are required for AR binding in an antagonist-related conformation. 1005 is a cinnamyl hydroxamic acid derivative with a three-carbon linker. A relatively longer carbon chain in 2-75 was used to more closely mimic the chemical structure of SAHA. Compound 7 (3-52), a close structural analogue of 2-75 using methyl ester to replace ZBG was synthesized as a control compound without an HDACi functional group (FIG. 1B). Compound 7 (3-52) and synthetic intermediate compound 2 (i.e. 1002, an ethyl ester analogue of 1005, FIG. 1A, 1B) were used to investigate AR antagonist properties of 2-75 and 1005 scaffold, respectively.

Both 2-75 and 1005 were synthesized from a 4'-iodo substituted intermediate (FIG. 1B) 1. Acrylate linker of 1005 was introduced via Pd(OAc)2-catalyzed Heck reaction to afford compound 2, followed by hydrolysis of ethyl ester, coupling to THP (tetrahydropyranyl acetal)-protected hydroxylamine and the final acidic deprotection. To synthesize 2-75, carboxylation of aryl iodine 1 was performed using a palladium-catalyzed carboxylation reaction (Cacchi et al., 2003), the resulted carboxylic acid then coupled with primary amines to attach the alkyl chain with protected hydroxamic acid (compound 6) or methyl ester (compound 7). Removal of THP protecting group gave the final product 2-75.

Example 2. Characterizing the Synthesized Compounds

The synthesized compounds were characterized as described below.

HDAC activity assay. In vitro HDAC inhibition was measured by using the HDAC fluorimetric assay/drug discovery Kit (Enzo Life Sciences, BML-AK500) and the HDAC6 fluorometric drug discovery kit (Enzo Life Sciences, BML-AK516) following the manufacturer's protocols and instructions. $IC_{50}$ values were calculated from nonlinear aggression plots using GraphPad Prism5 software.

Cell Culture and Reagents. LNCaP and 22Rv1 cell lines were from American Type Culture Collection (Manassas, Va.). C4-2 cells were kindly provided by Dr. Edwin Sanchez (University of Toledo). LNCaP and C4-2 cells were routinely grown at 37° C. in 5% $CO_2$ in RPMI 1640 medium supplemented with 10% FBS (Invitrogen); 100 units/ml penicillin, 100 μg/ml streptomycin, 2 mM L-glutamine mixture (Invitrogen); and sodium pyruvate (1 mM) (Invitrogen). 22Rv1 cells were grown in RPMI 1640 medium supplemented with 10% FBS (Invitrogen); 100 units/ml penicillin, 100 μg/ml streptomycin, 2 mM L-glutamine mixture (Invitrogen). Affinity-purified rabbit anti-human antibody to AR (sc-816) and mouse anti-human antibody to GAPDH (sc-47724) were purchased from Santa Cruz Bio-technology (Santa Cruz, Calif.). Affinity-purified rabbit anti-human antibody to Hsp90 (C45G5) #4877 and rabbit anti-human antibody to acetylated lysine #9441 were purchased from Cell Signaling Technology. R1881 was kindly provided by Dr. Stephan Patrick (Karmanos Cancer Institute). All experiments were conducted using phenol-red free growth media. For hormone depletion, cells were grown in phenol-red free RPMI 1640 medium supplemented with 10% charcoal stripped FBS (Sigma-Aldrich) which was heat inactivated at 56° C. for thirty minutes, and a mixture of 100 units/ml penicillin, 100 µg/ml streptomycin and 2 mM L-glutamine for 96 h.

Lentivirus-mediated Transduction and shRNA Plasmids. shRNAs targeting AR and non-targeting control shRNA in the lentiviral expression vector pLKO.1-puro were purchased from Sigma Aldrich. For lentivirus-mediated gene knockdown, shrRNA targeting AR and non-targeting control shRNA were packaged in 293FT cells using lentiviral packaging plasmids; pMD2G, PMDLgg/RRE, and pRSV/REV. After 48 h and 72 h of transfection, the supernatant containing the virus was harvested, filtered and stored at −80° C. until the time of infection. $5 \times 10^5$ of 22Rv1 cells were plated in poly-D-lysine-coated 6-well plates in phenol red-free RPMI supplemented with 10% heat-inactivated charcoal-stripped FBS and 2 mM L-glutamine. The cells were infected twice over a 10 h period (Patki et al., 2013).

Cell Proliferation Assay. Cells were trypsinized and 6000 cells/well were seeded in 96-well plates coated with poly-D-lysine. The cells were seeded in phenol red-free medium supplemented with 10% FBS, 100 units/ml penicillin, 100 µg/ml streptomycin, 2 mM L-glutamine mixture and sodium pyruvate (1 mM) for C4-2 cells and phenol red-free medium supplemented with 10% FBS, 100 units/ml penicillin, 100 µg/ml streptomycin and 2 mM L-glutamine mixture for 22Rv1 cells. The cells were grown at 37° C. in 5% $CO_2$. Twenty four hours after seeding in the 96-well plates, the cells were treated with indicated compound or DMSO (vehicle). The culture medium was not changed during the time course of the assay. On Day zero and on Day 3, cell viability was determined using the MTT assay. MTT (10 µL, 5 mg/mL) was added to each well and incubated for 2 h at 37° C. The formazan crystal sediments were dissolved in 100 µL of DMSO, and the absorbance at 570 nm was measured using the BioTek Synergy 2 Microplate Reader (BioTek, Winooski, Vt.). The assay was conducted in sextuplicate wells and values were normalized to day zero (Patki et al., 2014). $IC_{50}$ values were calculated from non-linear aggression plots using GraphPad Prism5 software.

Western Blot Analysis. Cells were washed once with phosphate buffered saline (PBS) and then lysed with RIPA buffer (150 mM NaCl, 1% Nonidet P-40, 0.5% sodium deoxycholate, 0.1% SDS, 50 mM Tris of pH 8.0) containing a protease inhibitor cocktail (Pierce, Thermo Fisher Scientific). The cell lysates were then incubated on ice for 40 minutes. Total protein concentrations were estimated using the Bradford Assay (Bio-Rad). Protein samples (10-40 ug) were heated at 95° C. for 5 minutes and resolved by electrophoresis on 8% polyacrylamide-SDS gels and electrophoretically transferred to PVDF membranes (Millipore, Billerica, Mass.). The membranes were then probed overnight at 4° C. with the appropriate primary antibody followed by the appropriate horseradish peroxidase-conjugated secondary antibody. The blots were then developed to visualize the protein bands using the HyGLO Chemiluminescent HRP Antibody Detection Reagent (Denville Scientific, Metuchen, NI) (Salazar et al., 2011).

RNA isolation, Reverse Transcription, and Real Time PCR. Total RNA was isolated from cells using the RNeasy Mini Kit (Qiagen). Reverse transcription PCR was then performed using 500 ng of total RNA with random primers and using the high-capacity complementary DNA Archive kit (Applied Biosystems). The complementary DNA from this reaction was measured using quantitative real time PCR using the StepONE Plus Real Time PCR system (Life Technologies Corporation, Carlsbad, Calif.). All reactions were performed in triplicate and normalized to glyceraldehyde-3-phosphate-dehydrogenase values in the same samples. All primers and Taqman probes were purchased from the applied Biosystems inventory (Invitrogen) (Patki et al., 2015).

Chromatin Immunoprecipitation (ChIP). C4-2 cells were treated with either vehicle, R1881 (1 nM or 10 nM), or 10 µM of each indicated compound for 2 h and then subjected to ChIP using anti-AR antibody (sc-816 from Santa Cruz, Calif.). The ChIP assay was performed using the EX ChIP chromatin immunoprecipitation kit (catalogue number 17-371 from Millipore, Temecula, Calif.) according to the vendor's protocol. The ChIP signals were measured by quantitative real time PCR analysis of the immunoprecipitated products. Each sample was tested in triplicate (Patki et al., 2013).

Statistical Analysis. All experiments were performed in triplicate groups and repeated at least three times. The error bars in all graphs represent the standard deviation. Statistical analysis was performed using one-way ANOVA with post-hoc and LSD (Least Square Differences) and/or T-test (McFall et al., 2015).

Figure 2A:
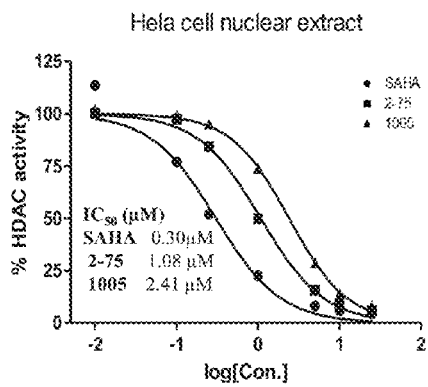
FIGS. 2A-2F show measurement of intrinsic and in situ HDACi activities. (2A) Dose-dependent inhibition of HDACs from Hela cell nuclear extract by 2-75, 1005 and SAHA. Hela cell nuclear extract was incubated with each drug at the indicated concentrations. IC$_{50}$ values were calculated from nonlinear regression plots using GraphPad Prism5 software. (2B) Enz, 1002 and 3-52 were tested against HeLa cell nuclear extract at 10 µM and 25 µM and TSA (1 µM) was used as positive control. (2C) Dose-dependent inhibition of recombinant HDAC6 by 2-75, 1005 and SAHA. Recombinant HDAC6 was incubated with each drug at the indicated concentrations. IC$_{50}$ values were calculated from nonlinear regression plots using GraphPad Prism5 software. (2D) Enz, 1002 and 3-52 were tested against recombinant HDAC6 at 10 µM and 25 µM and TSA (1 µM) was used as positive control. (2E) LNCaP cells were treated with the indicated compounds (10 µM) or vehicle (DMSO) for 48 h. Cells were then harvested to quantify mRNA for DLC1 and values were normalized to the values for GAPDH mRNA. (2F) C4-2 cells were treated with the indicated concentrations of Enz, SAHA, 2-75 or 1005 or vehicle (DMSO) for 48 h. Cells were then harvested to quantify mRNA for DLC1 and values were normalized to the values for GAPDH mRNA. In all panels (2A-2F), the error bars represent standard deviation of experimental triplicates. *$P<0.001$ FIGS. 3A-3C provide data showing testing the ability of compounds to interact with AR and to induce chromatin association of AR. (3A and 3B) Data obtained using C4-2 cells. After 96 h of hormone depletion cells were treated with R1881 (1 nM) and 1 µM, 2.5 µM, 5 µM, or 10 µM of the indicated compound or vehicle (DMSO) for 48 h. Cells were then harvested to purify total RNA. The mRNAs for KLK3 and TMPRSS2 were quantified by normalizing to the values for GAPDH mRNA. (3C) C4-2 cells plated in hormone-depleted medium were treated with either vehicle, R1881, or the indicated compound for 2 h. Cells were harvested and subjected to ChIP using AR antibody. Taqman probes targeting ARE enhancer elements associated with the KLK3 gene were used to quantify the immunoprecipitated chromatin. In all panels (3A-3C), the error bars represent standard deviation of experimental triplicates. In all panels (3A-3C), the error bars represent standard deviation of experimental triplicates. *P<0.001
Figure 2B:
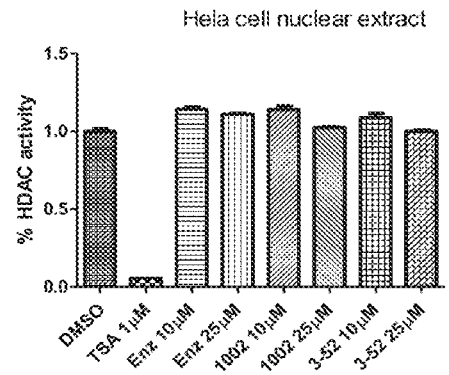
Figure 2C:
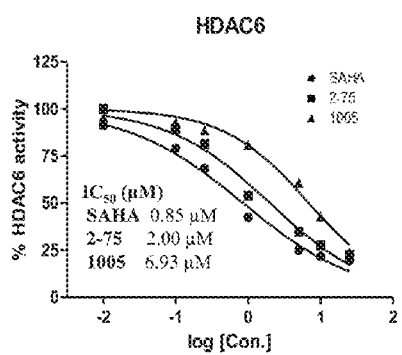
Figure 2D:
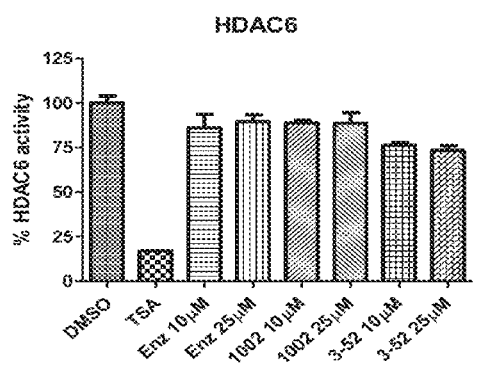

Compounds 2-75 and 1005 possess intrinsically weak inhibitor activity against nuclear HDACs and cytosolic HDAC6. To measure HDAC inhibitory activities of 2-75 and 1005, cell-free enzymatic assays were performed against a nuclear extract of Hela cells and also against human recombinant HDAC6. HDAC1 and HDAC2 are enriched in nuclear extracts whereas HDAC6 is a cytosolic enzyme that is the principal modulator of the acetylation status of Hsp90. The HeLa cell nuclear extract was used to evaluate inhibitory activity against nuclear HDACs. 2-75 and 1005 dose-dependently inhibited HDACs enriched in the Hela nuclear extract with $IC_{50}$ values of 1.08 µM and 2.41 µM compared to a value of 0.30 µM for SAHA (FIG. 2A). In contrast, compounds 3-52 and 1002, which share the chemical scaffolds of 2-75 and 1005 respectively, but lack the HDACi functional group, did not inhibit nuclear HDAC activity even up to a concentration of 25 µM (FIG. 2B). As expected, Enz also lacked any HDACi activity in contrast to a pan-HDACi, trichostatin A (TSA), which was used as a positive control (FIG. 2B). 2-75 and 1005 were also weaker inhibitors of recombinant HDAC6, with $IC_{50}$ values of 2.0 µM and 6.93 µM, respectively compared with the $IC_{50}$ of 0.85 µM for SAHA (FIG. 2C). As expected, the negative control compounds 3-52 and 1002 as well as Enz did not show significant inhibitory activity against HDAC6 even at a concentration of 25 µM (FIG. 2D). Again, TSA served as the positive control in FIG. 2D.

Figure 2E:
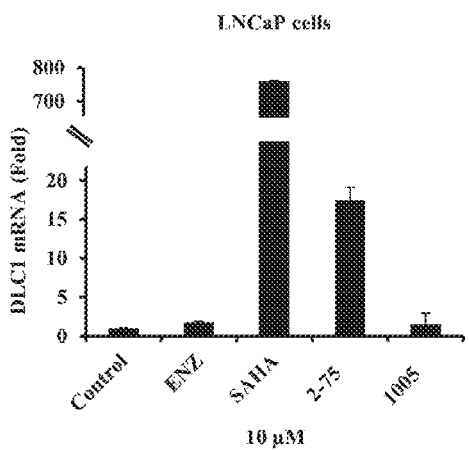
Figure 2F:
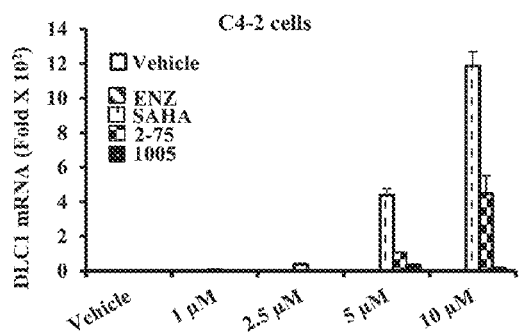

The HDACi activities of 2-75 and 1005 were also compared with those of their parent compounds in situ in both LNCaP and C4-2 prostate cancer cells using activation of the DLC1 tumor suppressor gene as the readout. SAHA induces histone acetylation at the DLC1 promoter and effectively increases DLC1 mRNA expression in prostate cancer cells (Zhou et al., 2012). Accordingly, DLC1 mRNA was strongly up-regulated by SAHA in both LNCaP cells (FIG. 2E) and in C4-2 cells (FIG. 2F). As expected from the fact that DLC1 is not an AR-regulated gene, Enz had no effect on DLC1 mRNA expression. Consistent with the results of the cell-free HDACi assays above, compounds 2-75 and 1005 were poor inducers of DLC1 mRNA compared with SAHA, both in LNCaP cells and in C4-2 cells (FIGS. 2E and 2F). Further, similar to the results from cell-free assays, 1005 was a much weaker HDACi than 2-75 in the in situ assays (FIGS. 2E and 2F). Taken together, the results indicate that compounds 2-75 and, to a greater degree, 1005 have much less potent HDACi activity in the cellular context reflecting their intrinsically weak inhibitor activities compared with SAHA.

Figure 3A:
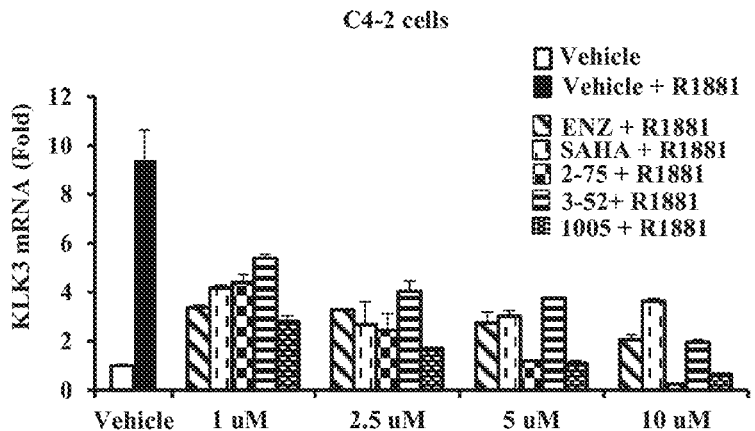
Figure 3B:
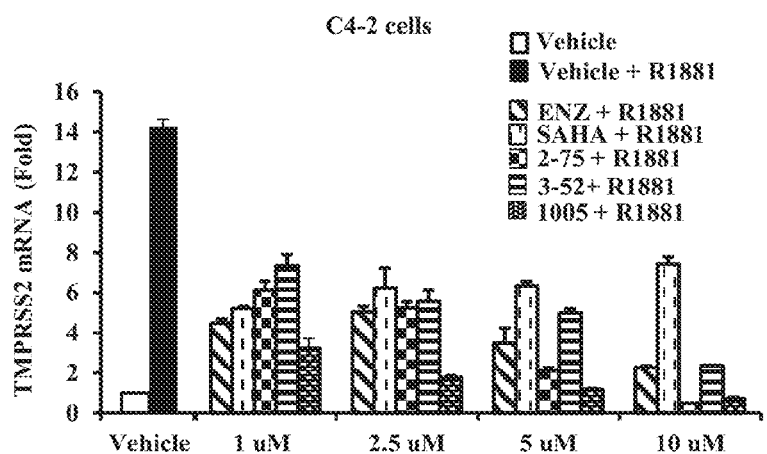

The partial Enz chemical scaffold confers AR targeted antagonist activity without ligand induced chromatin association of AR. Although C4-2 cells are not growth-inhibited by Enz due to hormone-independent actions of AR the canonical androgen target genes Kallikrein-related Peptidase 3 (KLK3) and transmembrane Protease, Serine 2 (TMPRSS2) are activated by androgen and their activation is inhibited by androgen antagonists (Ratnam et al., 2013). HDACi are also potent inhibitors of the androgen signaling axis as they cause degradation of AR in the cytosol in addition to other cellular effects (Chen et al., 2005; Gravina et al., 2013; Gryder et al., 2013). To test whether the Enz moiety could enable 2-75 and 1005 to target to AR, the ability of compound 3-52 to inhibit activation of KLK3 and TMPRSS2 by androgen was tested. Compound 3-52 shares the chemical scaffold of 2-75 but lacks the HDACi functional group; therefore 3-52 should depend on the partial Enz chemical scaffold to antagonize gene activation by androgen. SAHA partially inhibited activation of KLK3 (FIG. 3A) and TMPRSS2 (FIG. 3B) by the synthetic androgen R1881 in C4-2 cells whereas Enz showed progressive inhibition at higher doses. Compounds 2-75 and 1005 were both better inhibitors of gene activation by androgen compared with either Enz or SAHA (FIGS. 3A and 3B). On the other hand, compound 3-52 inhibited activation of KLK3 and TMPRSS2 to a degree that was comparable to Enz suggesting that the partial Enz chemical scaffold in compounds 2-75 and 1005 retained an Enz-like AR binding property. The superior androgen antagonist activities of 2-75 and 1005 compared with Enz may be explained by their additional HDACi activities.

Figure 3C:
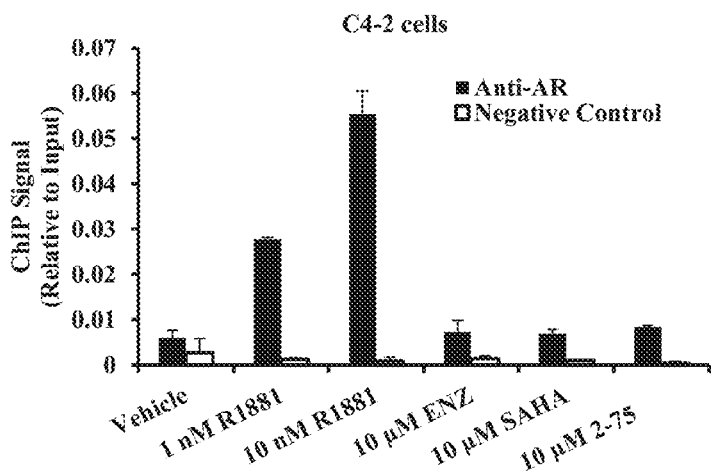

AR ligands including agonists and classical androgen antagonists such as bicalutamide promote nuclear translocation of AR and the binding of AR to canonical hormone (androgen) response elements associated with androgen-regulated genes. In contrast, Enz does not stimulate AR nuclear translocation and DNA binding (Guerrero et al., 2013; Tran et al., 2009). To test whether the partial Enz chemical scaffold would mobilize AR to the chromatin, chromatin immunoprecipitation using C4-2 cells treated with androgen, Enz, SAHA and compound 2-75 was employed. As a target site for the ChIP assay, the well-established AR binding enhancer elements located 4 kb upstream of the transcription initiation site of the KLK3 gene was chosen. As seen in FIG. 3C, androgen treatment strongly stimulated chromatin association of AR whereas Enz, SAHA and compound 2-75 all gave the basal ChIP signal corresponding to the vehicle treatment control. These results suggest that the new compounds must antagonize AR in the cytosolic rather than in the nuclear compartment.

Compounds 2-75 and 1005 induce enhanced degradation of AR and Hsp90 and hyper-acetylation in a putative 55 KDa Hsp90 fragment. Previous observations using potent non-targeted HDACi have shown that the compounds directly affect the AR signaling axis by hyper-acetylation of the AR chaperone complex, through inhibition of HDAC6, leading to degradation of Hsp90 as well as release and degradation of AR. It was therefore hypothesized that despite their intrinsically weak HDACi activities, the Enz moiety may enable compounds 2-75 and 1005 to more effectively target AR in its chaperone complex, leading to relatively efficient degradation of AR. To test this possibility, C4-2 cells were treated with Enz, SAHA, 1005 and 2-75 at doses ranging from 1 µM to 10 µM for 24 h. Western blots of the cell lysates were probed for AR and GAPDH (loading control) and the AR band intensities relative to GAPDH were quantified using ImageJ software (FIG. 4A). Whereas Enz did not cause an appreciable change in the AR protein level, SAHA did induce degradation of AR in a dose-dependent manner (FIG. 4A). Compared to SAHA, both 2-75 and 1005 more efficiently induced AR protein degradation with 2-75 being more effective than 1005 at each dose (FIG. 4A). The extent of degradation of AR in C4-2 cells appeared adequate to offset the high level of overexpression of AR that is necessary to support growth in these cells.

To explore a possible link between decreased AR levels and effects of the compounds on the AR chaperone complex, whether compounds 2-75 and 1005 induced degradation of Hsp90 was examined. As Hsp90 associated with the AR chaperone complex is a part of the total cellular pool of Hsp90, degradation of all of the Hsp90 in this experiment would not be expected. Probing of the lysates from the treated cells for Hsp90 by western blot and quantification of Hsp90 was conducted by procedures similar to that used above for AR. Enz had no effect on the level of Hsp90 whereas in the SAHA-treated cells, a decrease in Hsp90 was evident at the higher doses (5 µM and 10 µM) (FIG. 4B). On the other hand, cells treated with 1005 and 2-75 showed more marked reduction in Hsp90, with 2-75 being more efficient than 1005. Probing identical western blots with an antibody against acetylated lysine showed that SAHA as well as 1005 and 2-75, but not Enz, showed hyper-acetylation of a 55 KDa polypeptide (FIG. 4C), similar to one that has previously been identified as a fragment Hsp90 produced by SAHA treatment (Park et al., 2015). Taken together, the above results are consistent with the view that the cytosolic AR chaperone complex is the target site of action of 1005 and 2-75. The ability of the compounds to induce acetylation and degradation of the AR chaperone protein Hsp90, and consequently AR degradation, underlies the ability of the compounds to attenuate AR signaling.

2-75 and 1005 up-regulate p21 and inhibit viability of Enz-resistant prostate cancer cells. HDACi activate transcription of p21. However, as compounds 2-75 and 1005 exhibited weak intrinsic HDACi activity against nuclear HDACs and as their apparent major cellular HDACi activity was related to targeting of the AR axis within the cytosolic compartment, it was of interest to examine their ability to induce p21.

Enz had no effect on p21 mRNA expression in either the Enz-sensitive LNCaP cells (FIG. 5A) or in the Enz-insensitive C4-2 cells (FIG. 5B), whereas SAHA induced p21 mRNA in both cell lines (FIGS. 5A and 5B). Compounds 2-75 and 1005 both induced p21 to a greater extent than SAHA in the two cell lines (FIGS. 5A and 5B). Moreover, combined treatment with equimolar concentrations of Enz and SAHA did not induce p21 to a greater extent than SAHA alone, indicating the importance of the hybrid scaffold of 2-75 and 1005 (FIG. 5C).

Next, the antiproliferative effects of 2-75 and 1005 vs. SAHA were assessed in two well established Enz-resistant advanced PCa cell line models, C4-2 and 22Rv1. C4-2 cells are resistant to Enz by virtue of their vast overexpression of AR that is able to support hormone-independent cell growth.

Figure 6A:
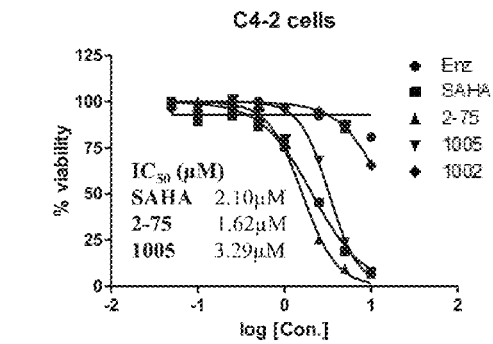
Figure 6B:
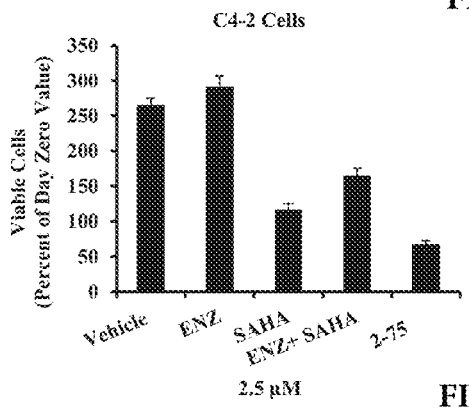
Figure 6C:
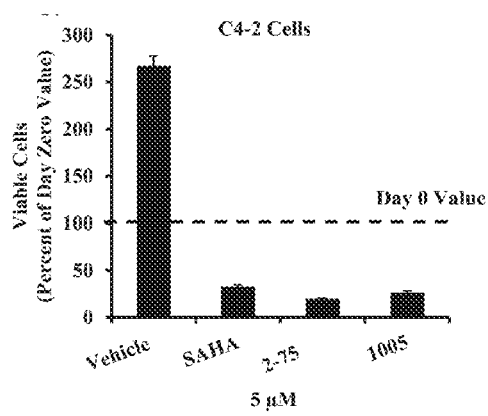

In C4-2 cells Enz could not appreciably affect growth even at a concentration of 10 µM, whereas SAHA inhibited cell growth in a dose dependent manner with an $EC_{50}$ value of 2.1 µM (FIG. 6A). Compound 1005 inhibited C4-2 cell growth ($EC_{50}$, 3.29 µM) to an extent comparable to SAHA, whereas compound 2-75 produced greater growth inhibition ($EC_{50}$, 1.62 µM) (FIG. 6A). As a control, compound 1002, which has a chemical scaffold similar to 1005 but lacks the HDACi activity (FIGS. 2B and 2D), was unable to appreciably inhibit C4-2 cell growth (FIG. 6A). A slight effect of 1002 on growth observed at the highest dose in FIG. 6A is likely because of some expected hydrolysis of the ethyl ester group within the cell, releasing a free carboxyl group that may be expected to confer a low level of HDACi activity. As another experimental control, combining Enz with SAHA did not enhance the ability of SAHA to inhibit cell growth (FIG. 6B). It is notable that similar to SAHA, 2-75 and 1005 did not merely cause growth inhibition but actually caused cell death as seen by a decrease in viable cells below the number on Day 0 of treatment (FIG. 6C); hence, the design of 2-75 and 1005 allowed them to retain the cytotoxic effect of SAHA despite their intrinsically weak HDACi activities.

Figure 6D:
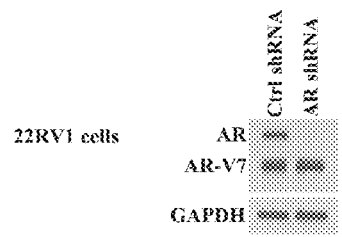
Figure 6D:
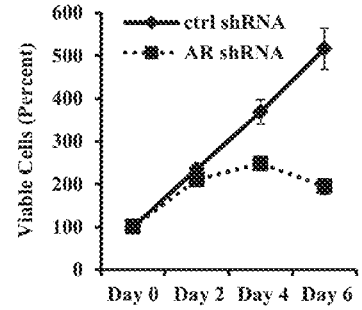
Figure 6E:
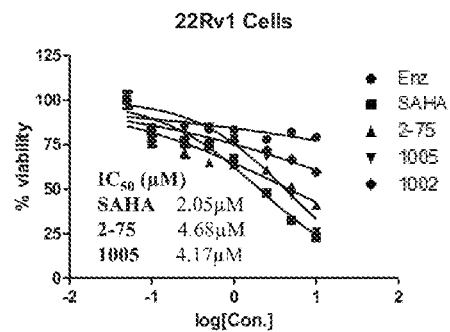

In the 22Rv1 model, hormone-independent growth is supported by overexpression of a major AR splice variant (AR-v7) (Yamashita et al., 2012), which has a carboxyl terminal truncation, resulting in loss of its ligand binding domain. However, it has been suggested that in PCa cells overexpressing AR splice variants, the truncated AR synergizes with relatively low levels of full length AR in supporting growth (Watson et al., 2010). 22Rv1 cells also express a low level of the full length AR (FIG. 6D, right panel). In 22Rv1 cells, the full length AR as well as AR-v7 were required for hormone-independent growth, as evident from the fact that selective knockdown of the full length AR (FIG. 6D, right panel) resulted in loss of cell growth in hormone-depleted media (FIG. 6D, left panel). Therefore the AR axis in 22Rv1 cells may also be expected to be targeted by 2-75 and 1005 via binding to the full length AR. SAHA ($EC_{50}$, 2.05 µM), 2-75 ($EC_{50}$, 4.68 µM) and 1005 ($EC_{50}$, 4.17 µM) but not Enz inhibited the growth of 22Rv1 cells while the control 1002 showed a modest effect at high concentrations (FIG. 6E).

The results indicate that despite the much weaker inherent HDACi activities of 2-75 and 1005 compared with SAHA, the compounds were as good or better inhibitors of viability of Enz-resistant PCa cells including those dependent on overexpression of the AR splice variant, AR-v7. Moreover, the functionally weak HDACi moieties of the new compounds and also their association with an Enz-like scaffold are necessary to inhibit viability.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. In particular embodiments, a material effect is a statistically signification reduction in the effectiveness of a drug disclosed herein to produce an anti-cancer effect in C4-2 cells.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

REFERENCES

Antonarakis, et al., (2014). The New England journal of medicine 371, 1028-1038.
Balbas, et al., (2013). Overcoming mutation-based resistance to antiandrogens with rational drug design. eLife 2, e00499.
Bali, et al., (2005). The Journal of biological chemistry 280, 26729-26734.
Basak, et al., (2008). Molecular cancer therapeutics 7, 3195-3202.
Beer, et al., (2014). The New England journal of medicine 371, 424-433.
Bhat, et al., (2014). Journal of medicinal chemistry 57, 8718-8728.
Bradley, et al., (2009). Cancer 115, 5541-5549.
Burdelski, et al., (2015). Experimental and molecular pathology 98, 419-426.
Cacchi, et al., (2003). Organic letters 5, 4269-4272.
Chen, et al., (2013). The Journal of Organic Chemistry 78, 5051-5055.
Chen, et al., (2005). Molecular cancer therapeutics 4, 1311-1319.
Chen, et al., (2009). The lancet oncology 10, 981-991.
Eigl, et al., (2015). Investigational new drugs 33, 969-976.
Fang, et al., (1996). The Journal of biological chemistry 271, 28697-28702.
Gartel & Tyner, (2002). Molecular cancer therapeutics 1, 639-649.
Gibbs, et al., (2009). Proceedings of the National Academy of Sciences of the United States of America 106, 16663-16668.
Gravina, et al., (2013). Endocrine-related cancer 20, 321-337.
Gryder, et al., (2013). ACS chemical biology 8, 2550-2560.
Guerrero, et al., (2013). The Prostate 73, 1291-1305.
He, et al., (2013). International journal of oncology 42, 35-43.
Heath, et al., (2008). Clinical cancer research: an official journal of the American Association for Cancer Research 14, 7940-7946.
Jiang, et al., (2013). Biochimica et biophysica acta 1833, 663-671.
Joseph, et al., (2013). Cancer discovery 3, 1020-1029.
Karantanos, et al., (2015). European urology 67, 470-479.
Kong, et al., (2012). Histone deacetylase inhibitors induce epithelial-to-mesenchymal transition in prostate cancer cells. PloS one 7, e45045.
Korpal, et al., (2013). Cancer discovery 3, 1030-1043.
Kovacs, et al., (2005). Molecular cell 18, 601-607.
Kramer, et al., (2014). Trends in pharmacological sciences 35, 501-509.
Li, et al., (2013). Cancer research 73, 483-489.
Liu, et al., (2014). Current pharmaceutical design 20, 2912-2921.
Liu, et al., (2015). Molecular pharmacology 88, 121-130.
Marrocco, et al., (2007). Molecular cancer therapeutics 6, 51-60.
McFall, et al., (2015). Oncotarget 6, 33146-33164.
Mitsiades, (2013). Cancer research 73, 4599-4605.
Molife, et al., (2010). Annals of oncology: official journal of the European Society for Medical Oncology/ESMO 21, 109-113.
Nakamura, et al., (2005). Endocrine-related cancer 12, 101-107.
Neckers & Workman, (2012). Clinical cancer research: an official journal of the American Association for Cancer Research 18, 64-76.
Oh, et al., (2011). Urology 78, 626-630.
Pacey, et al., (2011). Clinical cancer research: an official journal of the American Association for Cancer Research 17, 1561-1570.
Park, et al., (2015). Cell stress & chaperones 20, 149-157.
Patki, et al., (2013). The Journal of biological chemistry 288, 11047-11065.

Patki, et al., (2014). Journal of thoracic oncology: official publication of the International Association for the Study of Lung Cancer 9, 519-526.

Patki, et al., (2015). Biochemical and biophysical research communications 457, 404-411.

Rathkopf, et al., (2013). Cancer chemotherapy and pharmacology 72, 537-544.

Ratnam, et al., (2013). Mechanisms of ARE-Independent Gene Activation by the Androgen Receptor in Prostate Cancer Cells: Potential Targets for Better Intervention Strategies. In Androgen-Responsive Genes in Prostate Cancer, (Springer), pp. 85-100.

Salazar, et al., (2011). Breast cancer research: BCR 13, R18.

Saporita, et al., (2007). The Prostate 67, 509-520.

Sato, et al., (2012). The Journal of urology 188, 2410-2418.

Scher, et al., (2012). The New England journal of medicine 367, 1187-1197.

Siegel, et al., (2015). Cancer statistics, 2015. CA: a cancer journal for clinicians 65, 5-29.

Solit, et al., (2002). 17-Allylamino-17-demethoxygeldanamycin induces the degradation of androgen receptor and HER-2/neu and inhibits the growth of prostate cancer xenografts. Clinical cancer research: an official journal of the American Association for Cancer Research 8, 986-993.

Tam & Weinberg (2013). Nature medicine 19, 1438-1449.

Thakur et al., (2015). A phase II trial of ganetespib, a heat shock protein 90 Hsp90) inhibitor, in patients with docetaxel-pretreated metastatic castrate-resistant prostate cancer (CRPC)—a prostate cancer clinical trials consortium (PCCTC) study. Investigational new drugs.

Tran, et al., (2009). Science 324, 787-790.

Uchida, et al., (2012). The Journal of biological chemistry 287, 4441-4450.

Veldscholte, et al., (1992). Biochemistry 31, 7422-7430.

Watson, et al., (2010). Proceedings of the National Academy of Sciences of the United States of America 107, 16759-16765.

Weichert, et al., (2008). British journal of cancer 98, 604-610.

Welsbie, et al., (2009). Cancer research 69, 958-966.

Yamashita, et al., (2012). Neoplasia 14, 74-83.

Zhou, et al., (2012). Biochemical and biophysical research communications 420, 325-330.

What is claimed is:

1. A drug of Formula (I) or Formula (II),

Formula (I)

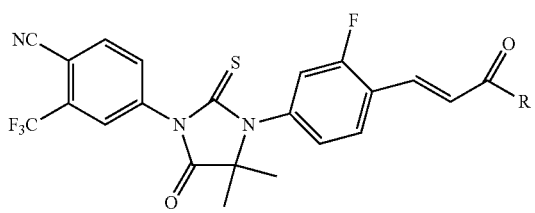

-continued

Formula (II)

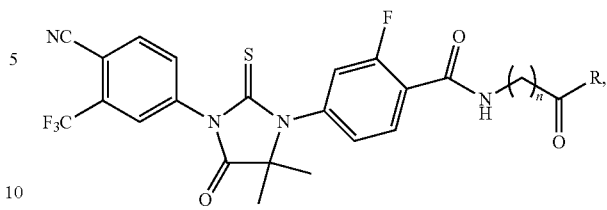

wherein:

n is 1 to 10; and

R is a hydrogen atom, a halogen atom, a hydroxyl group, a nitro group, an amino group, an alkyl group, a cycloalkyl group, an alkenyl group, an alkynyl group, an alkoxy group, an aryl group, an aralkyl group, or a heterocyclic group.

2. The drug of claim 1, wherein R is —NHOH.

3. The drug of claim 1, wherein the drug has Formula (II) and wherein n is 6 and R is —NHOH.

4. A pharmaceutical composition comprising the drug of claim 1 and a pharmaceutically acceptable carrier.

5. A method of providing an anti-cancer effect in a subject having androgen receptor (AR) positive cancer, wherein the method comprises administering a therapeutically effective amount of the pharmaceutical composition of claim 4 to the subject, thereby providing an anti-cancer effect in the subject.

6. The method of claim 5, wherein the AR positive cancer is prostate cancer or breast cancer.

7. The method of claim 6, wherein the prostate cancer is castration-resistant prostate cancer (CRPC).

8. The method of claim 5, wherein the pharmaceutical composition further comprises an additional active ingredient.

9. The method of claim 5, wherein the pharmaceutical composition is administered in conjunction with a second pharmaceutical composition comprising an active ingredient.

10. The method of claim 9, wherein the pharmaceutical composition and the second pharmaceutical composition are administered simultaneously or sequentially.

11. A method of inhibiting growth of AR positive cancer cells, wherein the method comprises contacting AR positive cancer cells with an effective amount of the drug of claim 1.

12. A method of degrading a full length androgen receptor (AR), wherein the method comprises contacting AR positive cancer cells expressing the full length AR with an effective amount of the drug of claim 1.

* * * * *